US012613179B2

(12) United States Patent
Hou et al.

(10) Patent No.: US 12,613,179 B2
(45) Date of Patent: Apr. 28, 2026

(54) LABEL-FREE ELECTRICAL MONITORING OF CELL AGGREGATES

(71) Applicant: NANYANG TECHNOLOGICAL UNIVERSITY, Singapore (SG)

(72) Inventors: Han Wei Hou, Singapore (SG); Lingyan Gong, Singapore (SG); Chayakorn Petchakup, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 594 days.

(21) Appl. No.: 18/022,002

(22) PCT Filed: Aug. 23, 2021

(86) PCT No.: PCT/SG2021/050492
§ 371 (c)(1),
(2) Date: Feb. 17, 2023

(87) PCT Pub. No.: WO2022/045971
PCT Pub. Date: Mar. 3, 2022

(65) Prior Publication Data
US 2023/0358664 A1    Nov. 9, 2023

(30) Foreign Application Priority Data
Aug. 28, 2020    (SG) ........................... 10202008339U

(51) Int. Cl.
| | |
|---|---|
| *G01N 15/1031* | (2024.01) |
| *B01L 3/00* | (2006.01) |
| *C12M 1/34* | (2006.01) |
| *C12M 1/42* | (2006.01) |
| *G01N 15/02* | (2006.01) |
| *G01N 15/10* | (2006.01) |
| *G01N 15/12* | (2024.01) |
| *G01N 33/50* | (2006.01) |
| *G01N 15/00* | (2006.01) |

(52) U.S. Cl.
CPC .... *G01N 15/1031* (2013.01); *B01L 3/502715* (2013.01); *C12M 41/46* (2013.01); *G01N 15/0266* (2013.01); *G01N 15/1023* (2024.01); *G01N 33/5011* (2013.01); *B01L 2300/0645* (2013.01); *B01L 2300/0816* (2013.01); *G01N 2015/0092* (2013.01); *G01N 2015/1029* (2024.01)

(58) Field of Classification Search
None
See application file for complete search history.

(56) References Cited

U.S. PATENT DOCUMENTS

| | | |
|---|---|---|
| 2006/0199173 A1 | 9/2006 | Thielecke et al. |
| 2009/0314066 A1 | 12/2009 | Nieuwenhuis et al. |
| 2014/0057283 A1 | 2/2014 | Wang et al. |

FOREIGN PATENT DOCUMENTS

| | | |
|---|---|---|
| EP | 2 259 044 A1 | 12/2010 |
| WO | WO 2020/058681 A1 | 3/2020 |
| WO | WO 2020/154566 A1 | 7/2020 |

OTHER PUBLICATIONS

Gawad et al., "Dielectric spectroscopy in a micromachined flow cytometer: theoretical and practical considerations", Lab on a Chip, vol. 4, pp. 241-251 (Year: 2004).*

Spencer et al., "Microfluidic impedance cytometry of tumour cells in blood", Biomicrofluidics, vol. 8, article 064124, pp. 1-12 (Year: 2014).*

Ayliffe, H.E., A.B. Frazier, and R.D. Rabbitt, "Electric impedance spectroscopy using microchannels with integrated metal electrodes," Journal of Microelectromechanical Systems, vol. 8, No. 1, Mar. 1999, pp. 50-57.

Bernabini, C., D. Holmes, and H. Morgan, "Micro-impedance cytometry for detection and analysis of micron-sized particles and bacteria," Lab on a Chip, 11, 2011, pp. 407-412.

Blicher, A., et al., "The temperature dependence of lipid membrane permeability, its quantized nature, and the influence of anesthetics," Biophysical Journal, vol. 96, Jun. 2009, pp. 4581-4591.

Chen, J., et al., "Microfluidic Impedance Flow Cytometry Enabling High-Throughput Single-Cell Electrical Property Characterization," International Journal of Molecular Sciences, 16, 2015, pp. 9804-9830.

De Ninno, A., et al., "Coplanar electrode microfluidic chip enabling accurate sheathless impedance cytometry," Lab on a Chip, 17, 2017, pp. 1158-1166.

De Ninno, A., et al., "High-throughput label-free characterization of viable, necrotic and apoptotic human lymphoma cells in a coplanar-electrode microfluidic impedance chip," Biosensors and Bioelectronics, 2020, 12 pages.

Dean, D.A., et al., "Electrical Impedance Spectroscopy Study of Biological Tissues," Journal of Electrostatics 66, 2008, pp. 165-177.

Ebrahimi, A., L.N. Csonka, and M.A. Alam, "Analyzing Thermal Stability of Cell Membrane of *Salmonella* Using Time-Multiplexed Impedance Sensing," Biophysical Journal 114, Feb. 6, 2018, pp. 609-618.

Frauenschuh, S., et al., "A microcarrier-based cultivation system for expansion of primary mesenchymal stem cells," Biotechnol Prog, 23, 2007, pp. 187-193.

(Continued)

*Primary Examiner* — Michelle F. Paguio Frising
(74) *Attorney, Agent, or Firm* — Nixon & Vanderhye P.C.

(57) ABSTRACT

A method of monitoring one or more cell aggregates, includes providing a flow path in which the one or more cell aggregates are in a medium and the flow path being configured to pass through a collective sensing zone of a set of electrodes, obtaining impedance-related signals corresponding to each of the medium and one of the one or more cell aggregates in the medium, and determining one or more electrical signatures for a cell aggregate, in which the one or more electrical signatures are based on impedance-related signals obtained from the set of electrodes. The method is one of dynamic testing at single-particle resolution. The electrical signatures may be an opacity and/or electrical size of the one or more cell aggregates, or electrical impedance spectroscopy-based electrical signatures. It is also to provide a microfluidic chip having a channel and electrodes for obtaining impedance-related signals.

20 Claims, 15 Drawing Sheets

(56) References Cited

OTHER PUBLICATIONS

Goh, T.K.-P., et al., "Microcarrier culture for efficient expansion and osteogenic differentiation of human fetal mesenchymal stem cells," BioResearch Open Access, vol. 2, No. 2, Apr. 2013, pp. 84-97.

Grossi, M. and B. Riccò, "Electrical impedance spectroscopy (EIS) for biological analysis and food characterization: a review," J. Sens. Sens. Syst., 6, 2017, pp. 303-325.

Hildebrandt, C., et al., "Detection of the osteogenic differentiation of mesenchymal stem cells in 2D and 3D cultures by electrochemical impedance spectroscopy," Journal of Biotechnology 148, 2010, pp. 83-90.

Hirschhaeuser, F., et al., "Multicellular tumor spheroids: an underestimated tool is catching up again," Journal of Biotechnology 148, 2010, pp. 3-15.

Hsu, C.Y.M., et al., "An Integrated Approach toward the Biomanufacturing of Engineered Cell Therapy Products in a Stirred-Suspension Bioreactor," Molecular Therapy Methods & Clinical Development, vol. 9, Jun. 2018, pp. 376-389.

Kieninger, J., et al., "Microsensor systems for cell metabolism—from 2D culture to organ-on-chip," Lab Chip, vol. 18, No. 9, May 7, 2018, pp. 1274-1291.

Kunz-Schughart, L.A., et al., "The Use of 3-D Cultures for High-Throughput Screening: The Multicellular Spheroid Model," Journal of Biomolecular Screening 9(4), 2004, pp. 273-285.

Küttel, C., et al., "Label-free detection of Babesia bovis infected red blood cells using impedance spectroscopy on a microfabricated flow cytometer," Acta Tropica 102, 2007, pp. 63-68.

Kutuk, O. and A. Letai, "Displacement of Bim by Bmf and Puma rather than increase in Bim level mediates paclitaxel-induced apoptosis in breast cancer cells," Cell Death and Differentiation, 17, 2010, pp. 1624-1635.

Li, B., et al., "Past, present, and future of microcarrier-based tissue engineering," Journal of Orthopaedic Translation, 3, (2015), pp. 51-57.

Mehta, G., et al., "Opportunities and challenges for use of tumor spheroids as models to test drug delivery and efficacy," Journal of Controlled Release, 164, (2012), pp. 192-204.

Neumann, T.V. and M.D. Dickey, "Liquid Metal Direct Write and 3D Printing: A Review," Advanced Materials Technologies, 5, 202000070, 2020, 16 pages.

Pan, Y., et al., "3D microgroove electrical impedance sensing to examine 3D cell cultures for antineoplastic drug assessment," Microsystems & Nanoengineering, 6:23, 2020, 10 pages.

Perez, E.A., "Paclitaxel in Breast Cancer," The Oncologist, 3, 1998. pp. 373-389.

Petchakup, C., et al., "Integrated inertial-impedance cytometry for rapid label-free leukocyte isolation and profiling of neutrophil extracellular traps (NETs)," Lab on a Chip, 19, (2019), pp. 1736-1746.

Petchakup, C., et al., "Label-free leukocyte sorting and impedance-based profiling for diabetes testing," Biosensors and Bioelectronics 118, (2018), pp. 195-203.

Petchakup, C., K. Li, and H. Hou, "Advances in Single Cell Impedance Cytometry for Biomedical Applications," Micromachines, 8, 87, (2017), 20 pages.

Raghavan, S., et al., "Comparative analysis of tumor spheroid generation techniques for differential in vitro drug toxicity," Oncotarget, vol. 7, No. 13, pages (2016), pp. 16948-16961.

Raicu, V. and Y. Feldman, Dielectric Relaxation in Biological Systems: Physical Principles, Methods, and Applications, Oxford University Press, 2015, 450 pages.

Schmid, Y.R.F., et al., "Electrical Impedance Spectroscopy for Microtissue Spheroid Analysis in Hanging-Drop Networks," ACS Sensors, 1, (2016), pp. 1028-1035.

Shirahama, H., et al., "Precise Tuning of Facile One-Pot Gelatin Methacryloyl (GelMA) Synthesis," Scientific Reports, 6:31036, DOI: 10.1038/srep31036, (2016), pp. 1-11.

Sun, T. and H. Morgan, "Single-cell microfluidic impedance cytometry: a review," Microfluidics and Nanofluidics, 8, (2010), pp. 423-443.

Tay, H.M., et al., "Rapid purification of sub-micrometer particles for enhanced drug release and microvesicles isolation," NPG Asia Materials, 9, e434, doi: 10.1038/am.2017.175, (2017), 10 pages.

Vinci, M., et al., "Advances in establishment and analysis of three-dimensional tumor spheroid-based functional assays for target validation and drug evaluation," 10:29, BMC Biology, (2012), 20 pages.

Wang, X., F.F. Becker, and P.R.C. Gascoyne, "Membrane dielectric changes indicate induced apoptosis in HL-60 cells more sensitively than surface phosphatidylserine expression or DNA fragmentation," Biochimica et biophysica acta, 1564, (2002), pp. 412-420.

Wood, D.K., et al., "A feasible approach to all-electronic digital labeling and readout for cell identification," Lab on a Chip, 7, (2007), pp. 469-474.

Wu, Q., et al., "Bionic 3D spheroids biosensor chips for high-throughput and dynamic drug screening," Microdevices, 20, (2018), 9 pages.

Yang, D. and Y. Ai, "Microfluidic impedance cytometry device with N-shaped electrodes for lateral position measurement of single cells/particles," Lab on a Chip, vol. 19, No. 21, Nov. 7, 2019, pp. 3609-3617.

Yang, D., et al., "Biophysical phenotyping of single cells using a differential multiconstriction microfluidic device with self-aligned 3D electrodes," Biosensors and Bioelectronics, 133, (2019), pp. 16-23.

Zasadil, L.M., et al., "Cytotoxicity of Paclitaxel in Breast Cancer Is due to Chromosome Missegregation on Multipolar Spindles," Science Translational Medicine, vol. 6, Issue 229, 229ra43, Mar. 26, 2014, 11 pages.

Zhao, X., et al., "Photocrosslinkable Gelatin Hydrogel for Epidermal Tissue Engineering," Advanced healthcare materials, 5, (2016, pp. 108-118.

International Search Report for PCT/SG2021/050492 mailed Nov. 12, 2021, 3 pages.

Written Opinion of the ISA for PCT/SG2021/050492 mailed Nov. 12, 2021, 7 pages.

Burgel et al., "Automated, Multiplexed Electrical Impedance Spectroscopy Platform for Continuous Monitoring of Microtissue Spheroids", Anal Chem, Sep. 21, 2016, vol. 88, No. 22, pp. 10876-10883.

Curto et al., "A Planar Impedance Sensor for 3D Spheroids", Lab Chip, Mar. 13, 2018, vol. 18, No. 6, pp. 933-943.

Luongo et al., "Microfluidic Device for Trapping and Monitoring Three Dimensional Multicell Spheroids Using Electrical Impedance Spectroscopy", Biomicrofluidics, Jun. 5, 2013, vol. 7, No. 3, pp. 1-12.

Wen et al., "Quantitative Measurement and Evaluation of Red Blood Cell Aggregation in Normal Blood Based on a Modified Hanai Equation", Sensors, Mar. 4, 2019, vol. 19, No. 5, article 1095, pp. 1-12.

Cheung et al., "Microfluidic Impedance-Based Flow Cytometry", Cytometry A, May 21, 2010, vol. 77A, No. 7, pp. 648-666.

Panwar et al., "Integrated Fusible Alloy Microelectrodes Based Microfluidic Impedance Cytometry for Cell-in-Droplet Quantification", Microelectronic Engineering, May 25, 2019, vol. 215, article 111010, pp. 1-18.

Gong et al., "Direct and Label-Free Cell Status Monitoring of Spheroids and Micorcarriers Using Microfluidic Impedance Cytometry" small, Mar. 24, 2021, vol. 17, No. 21, article 2007500, pp. 1-11.

Alexander, "RTEMIS: Real-Time Tumoroid and Environment Monitoring Using Impedance Spectroscopy and pH Sensing", University of South Florida, Scholar Commons, Graduate Theses and Dissertations, Jun. 9, 2014, 151 pages.

Panwar et al., "Integrated Field's metal microelectrodes based microfluidic impedance cytometry for cell-in-droplet quantification", Microelectronic Engineering 215, 2019, pp. 1-8.

Search Report dated Apr. 16, 2024 in Singapore Application No. 11202301148P, 3 pages.

Written Opinion dated Apr. 17, 2024 in 11202301148P, 8 pages.

Extended European Search Report mailed Jul. 8, 2024 in European Application No. 21862210.8, 9 pages.

* cited by examiner

500

Detachably seal one end of each slot with aluminum foil    ~520

Fill each slot with flowable metal    ~530

Separate aluminum foil from the electrode layer    ~540

Assemble electrode layer and channel layer to form a channel with electrodes    ~550

LABEL-FREE ELECTRICAL MONITORING OF CELL AGGREGATES

This application is the U.S. national phase of International Application No. PCT/SG2021/050492 filed Aug. 23, 2021 which designated the U.S. and claims priority to SG 10202008339U filed Aug. 28, 2020, the entire contents of each of which are hereby incorporated by reference.

TECHNICAL FIELD

The present disclosure relates to electrical-based monitoring of cell aggregates, and more particularly to impedance monitoring of 3D cell aggregates.

BACKGROUND

Conventional methods of studying cell cultures in the laboratory may not translate easily into scaled-up biomanufacturing or in bioreactors for industrial processes. For example, in optical fluorescence microscopy, a cell aggregate is dissociated into single cells, stained with fluorescent dyes, and studied under the microscope. Such methods are invasive and destructive (to both the individual cells and the integrity of the cell aggregate) and difficult to efficiently implement in large scale bioprocesses. Conventional methods seek to probe changes in the properties of the culture medium. For example, samples of the culture medium may be measured for changes in temperature, dissolved oxygen, and pH (acidity/alkalinity).

SUMMARY

In one aspect, the present disclosure provides a method of monitoring one or more cell aggregates, the method comprising: providing a flow path of the one or more cell aggregates are in a medium, the flow path being configured to pass through a collective sensing zone of a set of electrodes; obtaining impedance-related signals from the collective sensing zone, the impedance-related signals corresponding to each of the medium and one of the one or more cell aggregates in the medium; and determining one or more electrical signatures for the cell aggregate, the one or more electrical signatures being based on impedance-related signals obtained from the set of electrodes. Optionally, the one or more electrical signatures are determined at single-particle resolution. Optionally, the flow path is configured such that the one or more cell aggregates are in a continuous flow mode in the collective sensing zone concurrently with the obtaining of the impedance-related signals.

The method as described above, wherein the impedance-related signals are obtained when the one or more cell aggregates are in motion relative to the set of electrodes.

The method as described above, further comprising: returning the one or more cell aggregates to a reservoir after the one or more cell aggregates have passed through the collective sensing zone.

The method as described above, wherein the one or more electrical signatures is one or more of an opacity of the one or more cell aggregates and an electrical size of the one or more cell aggregates.

The method according to any described above, wherein the opacity is a ratio between a first impedance and a second impedance, and wherein the first impedance is obtained at a higher frequency than the second impedance. The first impedance and the second impedance may be obtained at a beta dispersion range of frequencies. The second frequency may be selected from a range of frequencies corresponding to impedance-related signals of the medium such that the second frequency corresponds to a minimum electrical double layer (EDL) effect.

The method according to any described above, wherein the electrical size is determined based on the second impedance.

The method according to any described above, wherein the one or more electrical signatures are EIS-based (electrical impedance spectroscopy-based) electrical signature.

The method according to any described above, wherein the one or more EIS-based electrical signatures are obtained from differential values between impedance-related signals measured at a first electrode and a second electrode, wherein the first electrode and the second electrode are selected from the set of electrodes.

The method according any described above, wherein the cell aggregate is in one of a first sensing zone and a second sensing zone, the first sensing zone being provided by the first electrode and a source electrode, the second sensing zone being provided by the second electrode and the source electrode, and wherein the first sensing zone and the second sensing zone form the collective sensing zone.

The method according to any described above, further comprising: determining state or a change in the state of the one or more cell aggregates based on the one or more electrical signatures, wherein the state includes a physiological and/or morphological state of the one or more cell aggregates.

The method according to any described above, further comprising: determining change in an optical size of the one or more cell aggregates based on the one or more electrical signatures.

The method according to any described above, further comprising: determining a change in a cell count of the one or more cell aggregates based on the one or more electrical signatures.

The method according to any described above, further comprising: determining a cell aggregate growth of the one or more cell aggregates based on the one or more electrical signatures.

The method according to any described above, further comprising: determining change in cell viability of the one or more cell aggregates based on the one or more electrical signatures.

The method according to any described above, further comprising: determining a change in health of the one or more cell aggregates based on the one or more electrical signatures.

The method according to any described above, further comprising: determining a cytotoxicity response of the one or more cell aggregates based on the one or more electrical signatures.

The method according to any described above, further comprising: determining a drug efficacy with respect to the one or more cell aggregates based on the one or more electrical signatures.

The method according to any described above, the method comprising: determining if the cell aggregate has increased in its optical size based on whether there is an increase in the electrical size and whether there is concurrently a relatively small change or no change in the opacity.

The method according to any described above, the method comprising: determining if cell proliferation has occurred in the cell aggregate based on whether there is a decrease in the opacity and whether there is concurrently an increase in the electrical size.

The method according to any described above, the method comprising: determining a decrease in cell viability based on whether there is an increase in the opacity and whether concurrently there is a decrease or no change in the electrical size, wherein the cell viability corresponds to one or more of the following: a decrease in a proportion of living cells, an increase in a proportion of dead cells, and a deterioration in a health of the cell aggregate.

The method according to any described above, the method comprising: determining drug susceptibility with respect to the cell aggregate based on whether there is a decrease in electrical size concurrent with a relatively small decrease or no change in the opacity.

The method according to any described above, wherein the cell aggregate is a spheroid, an encapsulated microcarrier, or a cell-adhered microcarrier.

In another aspect, the present disclosure provides a system, the system comprising: at least one reservoir configured to culture one or more cell aggregates; at least one monitoring device having a set of electrodes configured to define a collective sensing zone; and a flow path defining a recirculating flow of the one or more cell aggregates between one of the at least one reservoir and the collective sensing zone of a corresponding one of the at least one monitoring device, wherein the at least one monitoring device is configured to monitor the one or more cell aggregates according to any method described above.

In another aspect, the present disclosure provides a microfluidic chip comprising: a channel; a source electrode excitable at a frequency; and a first electrode spaced apart from the source electrode, the source electrode and the first electrode being disposed in the channel and configured to provide at least part of a collective sensing zone, wherein the channel is configured to enable one or more cell aggregates to move through the collective sensing zone in turn to be monitored according to any method described above.

The microfluidic as described above, further comprising: a second electrode disposed in the channel and spaced apart from the source electrode, wherein in operation, the first electrode and the second electrode are spaced apart along the channel to provide a differential value based on impedance-related signals obtainable at the first electrode and the second electrode.

In another aspect, the present disclosure provides a method making the microfluidic chip according to any described above, the method comprising: detachably sealing one end of each of a plurality of slots defined in an electrode layer with an aluminum foil under an electrode layer; filling each slot with a flowable metal to form a set of electrodes in the electrode layer; separating the aluminum foil from the electrode layer after solidification of the flowable metal; and assembling the electrode layer with a channel layer to form a channel such that the set of electrodes are disposed in the channel.

DETAILED DESCRIPTION

Reference throughout this specification to "one embodiment", "another embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment. Furthermore, the described features, structures, or characteristics may be combined in any suitable manner in one or more embodiments. In the following description, numerous specific details are provided to give a thorough understanding of embodiments. One skilled in the relevant art will recognize, that the various embodiments be practiced without one or more of the specific details, or with other methods, components, materials, etc. In other instances, some or all known structures, materials, or operations may not be shown or described in detail to avoid obfuscation.

The word "exemplary" is used herein to mean "serving as an example, instance, or illustration." Any embodiment described herein as "exemplary" is not necessarily to be construed as preferred or advantageous over other embodiments. As used herein, the singular 'a' and 'an' may be construed as including the plural "one or more" unless apparent from the context to be otherwise.

Terms such as "first" and "second" are used in the description and claims only for the sake of brevity and clarity, and do not necessarily imply a priority or order, unless required by the context. The terms "about" and "approximately" as applied to a stated numeric value encompasses the exact value and a reasonable variance as will be understood by one of ordinary skill in the art, and the terms "generally" and "substantially" are to be understood in a similar manner, unless otherwise specified.

Figure 1A:
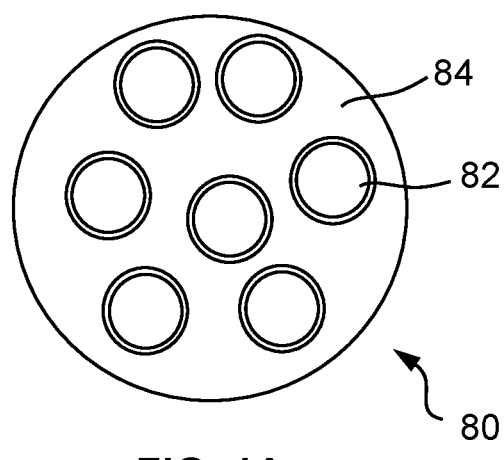
FIGS. 1A to 1C are schematic representations of different types of cell aggregates.
Figure 1B:
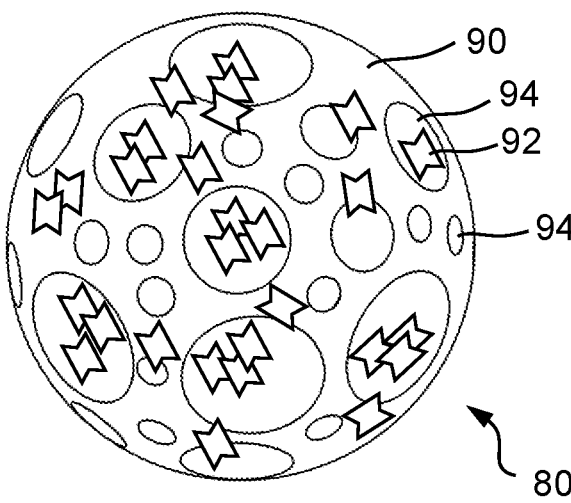
Figure 1C:
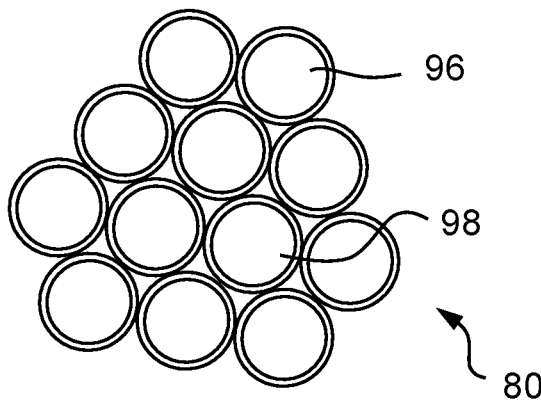

In the present disclosure, the term "cell aggregate" refers generally to a group of multiple cells adhered, clustered, anchored or otherwise congregated together. Cell aggregates 80 may be of various different sizes, and some of them are more than 100 μm in size, as compared to a cell which may be about 10 μm to 30 μm in size (diameter). Some cell aggregates are anchorage-dependent, with cells disposed on/in a microcarrier in a monolayer or in 3D (multiple cell layers). Microcarriers come in various configurations and may be shaped and sized according to the type and purpose of the cell culture, or according to the type of tissue being mimicked. Some microcarriers are spherical and suspended in a culture medium, such as hydrogel microcarriers, with cells (82) growing on a surface (84) of the microcarriers (as schematically illustrated in FIG. 1A). Some cell aggregates (80) are grown with microcarriers (90) are porous to enable cells (92) on a scaffold or in the pores (94) of the scaffold (FIG. 1B). The term "cell aggregates" (80) as used in the present disclosure may also refer to spheroids, i.e., self-organizing clusters of cells (96/98) that form generally spheroid-shaped aggregates, in free suspension in a culture medium without the aid of microcarriers (FIG. 1C). Some cells (98) positioned in an inner part of a spheroid may therefore have a slower diffusion of metabolites to the extracellular environment, compared to other cells (96) that are positioned on the outer surface of the spheroid. Cell culture of three-dimensional (3D) cell aggregates enable better understanding of intercellular and/or extracellular (cell-matrix) interactions and complexities, compared to two-dimensional (2D) monolayer cell culture techniques. 3D cell aggregates are comparatively better representations of the in vivo environment, and hence better models for cytotoxicity or drug efficacy assessments, studying tumor properties, etc. 3D cell aggregates are also increasingly important in scaled-up bioprocesses or biomanufacturing, e.g., in protein production, vaccine production, tissue engineering, production of materials for cell therapy, and other biologics. However, owing to the more complex structure or architecture of cell aggregates (as compared to a single cell or to a monolayer of single cells), methods used in conventional single cell assays are generally not useful for testing cell aggregates, especially in the context of scaled-up or industrial bioprocesses.

The nature or structure of the cell aggregate makes it difficult to determine some types of information about the cell aggregate. Optical imaging of a cell aggregate can be particularly challenging as light and fluorescent dyes may not reach cells in the inner parts of the cell aggregates. It is also difficult to use optical inspection to accurately determine whether cell proliferation has occurred, because some of the cells may be hidden from view, e.g., hidden inside pores of a microcarrier or hidden under the outermost layer of cells. In order to determine whether cell proliferation has occurred, conventional fluorescence flow cytometry requires the cell aggregate to be dissociated into individual cells, so that the number of individual cells can be counted. In this sense, it is destructive because once a particular cell aggregate is used in testing, the resulting single cells become useless for the original purpose of the bioprocess.

Conventional electrical impedance spectroscopy (EIS) allows impedance measurement of 2D cell layers or 3D cell aggregates in static and low-throughput conditions. While conventional EIS can provide label-free testing of cells, it is also generally considered a relatively time-consuming technique. For example, in order to carry out conventional EIS, cell aggregates are trapped in cavities or in hanging droplets (generally referred to as "static" testing), and measurements can be taken. Understandably, static cell testing can examine only one to 10 spheroids at a time, which is not efficient enough for scaled-up industrial bioprocesses.

Conventionally, EIS alone is deemed inadequate for assessing the pathology associated with morphological changes of cell aggregates, for example, in the monitoring of tumoroids, EIS tests are supplemented by other types of tests such as pH sensing of the culture medium (extracellular environment). In some cases, conventional EIS is supplemented with the measurement of glucose or carbon dioxide concentrations in the culture medium to check if the cells in the culture are still viable. To monitor growth, the cell metabolites in the culture medium are measured. Such methods are indirect testing methods (measuring the cell culture rather than the cell aggregate) and hence not "real-time". Owing to limitations in the rate at which cell metabolites can diffuse into the culture medium, there is an inevitable delay between a change in the cell aggregate and a detectable change in the culture medium. It is also possible that the way metabolites diffuse into the culture medium vary among cells located at different parts of the same cell aggregate, e.g., some cells may have less direct contact with the culture medium while some cells have more surface area exposed to the culture medium.

The present disclosure proposes at least one electrical signature that can be used for characterizing multiple properties of cell aggregates, in which the electrical signature is based on readings or signals obtainable from electrical impedance spectroscopy (EIS) alone, without the need for supplementary data from testing the extracellular environment. For the sake of brevity, in the present disclosure, the term "EIS-based" refers to a value, parameter, measurement, signal, range, trend, etc., that is determined based on readings or signals obtainable from electrical impedance spectroscopy alone, without the need for supplementary data from testing the extracellular environment through non-EIS physical and/or chemical testing. In some embodiments, it is proposed to use two electrical signatures to characterize multiple properties of cell aggregates, in which both of the electrical signatures are EIS-based electrical signatures. In some embodiments, the electrical signatures include opacity. In some embodiments, the electrical signatures include electrical size. In some embodiments, the electrical signatures are used in combination to derive a physiological and/or morphological state of one or more cell aggregates. In some embodiments, the electrical signatures are used in combination to derive a change in the physiological and/or morphological state of one or more cell aggregates. The direct testing of the cell aggregate without reliance on indirect testing of metabolites in the culture medium enables the present method to provide "real-time" test data. In some embodiments, the two electrical signatures are obtainable from dynamic EIS testing of cell aggregates. The one or more electrical signatures are obtained from dynamic testing, i.e., testing conducted with the subject being tested in motion. According to embodiments of the present disclosure, one or more electrical signatures can be determined at single-particle resolution, or the obtaining of impedance-related signals can be performed at single-particle resolution, even though the one or more cell aggregates are concurrently in a continuous flow mode. In the present disclosure, dynamic testing includes testing one or more cell aggregates while they are being moved along a flow path, i.e., when the one or more cell aggregates are in a continuous flow mode. Particles (i.e., particles under test, such as cell aggregates etc.) can also be described as being in a continuous flow mode when the particles are being carried by, suspended in, or generally being in a medium which is being pumped through the flow path. The exact state of particles at the time of testing may vary from particle to particle, from time to time, etc. In the present disclosure, reference to the particles being "in the medium" is to be understood in general terms, without limiting the particles to a specific state or being in motion at a specific velocity. The terms "medium" and "culture medium" are also used interchangeably to refer to the blank medium, i.e., when the medium alone is being tested/measured without influence from any cell aggregate. Dynamic testing can also be described as testing that occurs (readings or measurements are taken) with the cell aggregate in motion relative to a sensor (electrodes), or when the cell aggregate is in a continuous flow mode. That is, test data is collected without intentionally immobilizing any of the cell aggregates before or during testing. The flow path of the one or more cell aggregates in the medium may be configured such that the one or more cell aggregates in the medium are in a continuous flow mode in the collective sensing zone, concurrently with the obtaining of the impedance-related signals. The term "concurrently" as used in the present disclosure refers to two or more events at least overlapping in time, regardless of whether the events start or end at the same time instant. Since the testing is wholly non-invasive and non-destructive (to both the single cell and the cell aggregate), the cell aggregates can be returned to the cell culture after being tested. The present method can be described as providing dynamic testing at a single-particle resolution, i.e., test data is obtained in connection with only one particle at any instant in time (single-particle resolution), while the particle or a plurality of the particles are in a continuous flow mode. In the present disclosure, single-particle resolution may refer to a resolution at a single cell aggregate level or at a single cell cluster level, depending on the context. The present method thus reduces wastage of the cell aggregates, and advantageously enables the same cell aggregates to be dynamically monitored over a long period of time, e.g., several days or even months.

In the present disclosure, the term "opacity" is proposed as a first electrical signature of a cell aggregate from which various properties of the cell aggregate can be determined. That is to say, the first electrical signature provides multiparametric information such that obtaining this one electrical signature alone can provide information on multiple parameters of the cell aggregate. Opacity can be derived from impedance-related signals obtained with respect to one or more cell aggregates, the one or more cell aggregates being in motion relative to a set of electrodes. Opacity, as described in the present disclosure, is an EIS-based electrical signature. Opacity may be determined as a ratio between a first impedance and a second impedance, in which the first impedance is measured at a higher frequency than the second impedance. Opacity may be represented by Equation (1) below:

$$Opacity = |Z_{HF}|/|Z_{LF}| \qquad \text{Equation (1)}$$

in which $|Z_{HF}|$ is the magnitude of an impedance obtained at a first frequency and $|Z_{LF}|$ is the magnitude of an impedance obtained at a second frequency, the first frequency being higher than the second frequency, and in which the first impedance and the second impedance are obtained with respect to one or more cell aggregates moving relative to a set of electrodes. In one example, one electrode is provided with a current at an excitation frequency, while readings or values are taken from another electrodes. In the present disclosure, the readings or values taken are referred to as impedance-related signals or impedance signals, for the sake of brevity. For the sake of brevity, in the present disclosure, the terms "first impedance" and "magnitude of the first impedance" will be used interchangeably, and likewise the terms "second impedance" and "magnitude of the second impedance" will be used interchangeably. Opacity may be expressed in terms of relative opacity to facilitate comparison. Relative opacity may be obtained by normalizing opacity, for example, with respect to the opacity of reference particles. Spherical polystyrene beads of about 250 μm in diameter may be used as reference particles, for example. In the present disclosure, the terms "opacity" and "relative opacity" may be used interchangeably.

In the present disclosure, electrical size is proposed as a second electrical signature of a cell aggregate from which various properties of the cell aggregate can be determined. The electrical size associated with a cell aggregate is proportional to a volume of the cell aggregate moving through a collective sensing region, and may be represented by the second impedance:

$$|Z_{LF}| = G \times d^3 \qquad \text{Equation (2)}$$

in which d represents a diameter of a cell aggregate and G is a specific factor ($V/\mu m^3$). The specific factor is determined from the impedance-related signals obtained for the reference particles, e.g., spherical polystyrene beads of about 250 μm in diameter. In the present disclosure, the terms "second impedance" and the "second electrical signature" are interchangeable. The electrical size, as described in the present disclosure, is another EIS-based electrical signature.

The first electrical signature and the second electrical signature may be used independently of each other or in conjunction with each other, to obtain information on multiple parameters describing the cell aggregate. A system of the present disclosure to monitor the cell aggregates can thus offer multiparametric monitoring without the need to undergo hardware reconfiguration and without the need to involve other invasive/destructive tests. The system may be programmed to offer the user the flexibility of choosing which one or more of multiple parameters to output, based on the electrical signatures obtainable from EIS signals.

The first frequency and the second frequency may be selected based on the electrical double layer (EDL) effect for the system, and in particular, at the surface of the electrodes used for obtaining the impedance-related signals. The actual frequencies used may thus vary among different embodiments that fall within the scope of the present disclosure. A system of the present disclosure may be calibrated with reference to the differential current and with reference to the impedance spectrum of the system without the cell aggregates (i.e., blank medium or the culture medium without the presence of the cell aggregates), to determine respective ranges of frequencies from which the first frequency and the second frequency may be selected. The system may also be calibrated in the sense of selecting the first frequency and the second frequency to be used.

As frequency increases, the effective relative permittivity generally decreases. The permittivity and the capacitance effect at a membrane varies with frequency, with different dielectric dispersion mechanisms dominating at different ranges of frequencies. As the frequency increases, the primary mechanism changes from α (alpha) dispersion to β (beta) dispersion, and from β (beta) dispersion to γ (gamma) dispersion. The first frequency is selected from a range of frequencies associated with β dispersion. The first frequency may be selected from a range of frequencies characterized by an upper bound frequency, in which upper bound frequency is defined as the highest frequency at which beta dispersion predominates.

In some embodiments, the first frequency is selected at (i.e., within or near) a beta dispersion range. In one example, a first frequency of 1 MHz is selected from a range between 0.5 MHz and 2.0 MHz. In some examples, the first frequency may be in the range from 0.5 MHz to 1.7 MHz. Theoretically, a higher frequency that is still within the beta dispersion may be selected. In practice, the selection of the first frequency may also take into consideration other considerations such as equipment dynamic operating range and background noise. The first frequency may be selected near the beta dispersion range as well as within the beta dispersion range.

Figure 2:
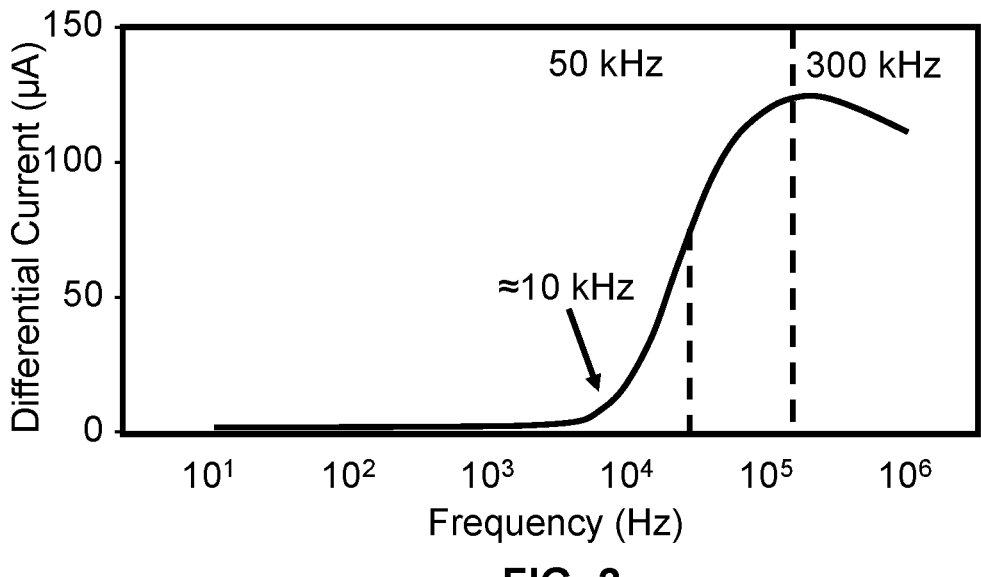
FIG. 2 is a plot of differential current against frequency.

A differential current may be plotted against frequency to determine a lower bound frequency for the second frequency. The differential current i may be determined according to Equation (3) below:

$$i = |1/Z_1| - |1/Z_2| \qquad \text{Equation (3)}$$

where $Z_1$ is the impedance detected across a pair of electrodes in the culture medium without the presence of a cell aggregate, and $Z_2$ is the impedance detected across the pair of electrodes in the culture medium in the presence of a cell aggregate. In other words, $Z_1$ is based on impedance-related signals corresponding to the medium (the blank medium alone). Strictly speaking, $Z_2$ is based on impedance-related signals corresponding to one or more cell aggregates and the medium in which the one or more cell aggregates are being suspended or carried in. Nevertheless, for the sake of clarity and brevity, in the present disclosure, $Z_2$ will be referred to as impedance-related signals corresponding to one of the one or more cell aggregates. The second frequency may be selected from a range of frequencies characterized by a lower bound frequency. In the example of FIG. 2, the second frequency may be selected to be higher than a lower bound frequency of about 10 kHz. In terms of the electrical double layer (EDL) effect, the differential current plot provides an indication of an operable range for the second frequency, in which the EDL impedance at the surface of the electrodes does not overwhelm or block the impedance sensing of the cell aggregate. The second frequency may be selected from a range of frequencies where the EDL effect is minimal.

Figure 3:
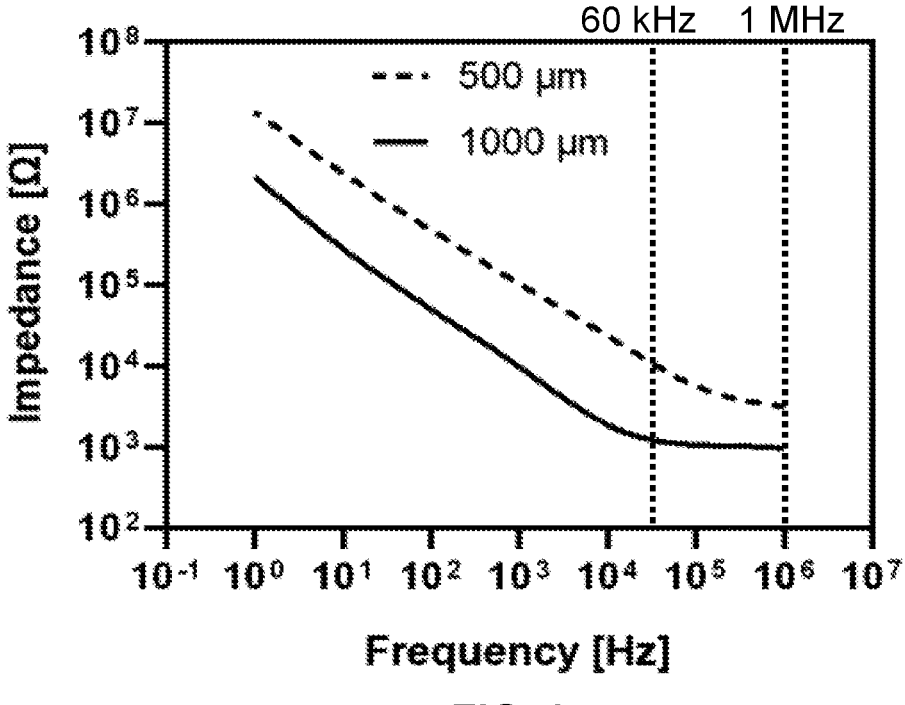
FIG. 3 is a plot of impedance against frequency.

The second frequency for a system to monitor the cell aggregates may also be determined with the aid of impedance spectrum plots or with reference to the impedance measured for a blank medium. The second frequency may be selected based on the impedance spectrum obtained from measuring the impedance of the culture medium (without the presence of the cell aggregates) over a range of frequencies. The second frequency can be set at the frequency at which the differential current is significantly smaller than at the first frequency (minimum EDL effect). FIG. 3 shows exemplary impedance spectra for two systems with different physical parameters, in particular, a system with a 500 μm-wide microfluidic channel and a system with a 1000 μm-wide microfluidic channel. In these examples, the second frequency may be selected from a range between 50 kHz and 200 kHz. In some examples, the second frequency is in a range from 50 kHz to 100 kHz. In this example, the second frequency is selected as 60 kHz when the impedance is less than 1% of the impedance at the first frequency of 1 MHz.

According to one embodiment of the present disclosure, a method includes determining one or more parameters related to properties or changes of one or more cell aggregates, in which the one or more parameters are determined based on EIS-based electrical signatures, for example, the opacity and/or the electrical size. Each of the opacity and the electrical size can be obtained from EIS signals when the one or more cell aggregates are in motion relative to the electrodes. The properties or changes of the one or more cell aggregates that can be monitored using these EIS-based electrical signatures include a state or a change in state related to pathological and/or morphological properties or characteristics of the one or more cell aggregates. The opacity may be defined as a ratio between a first impedance and a second impedance, and wherein the first impedance is obtained at a higher frequency than the second impedance, and wherein the first impedance and the second impedance are obtained at (i.e., within or near) a beta dispersion range of frequencies. The electrical size is determined based on the second impedance. In the present disclosure, obtaining the first impedance and/or the second impedance at a beta dispersion range of frequencies include obtaining the impedance within or near the beta dispersion range of frequencies. For the purpose of the present disclosure, an impedance is obtained "near" the beta dispersion range of frequencies if the impedance obtained is representative of impedances within the beta dispersion range of frequencies.

Figure 4A:
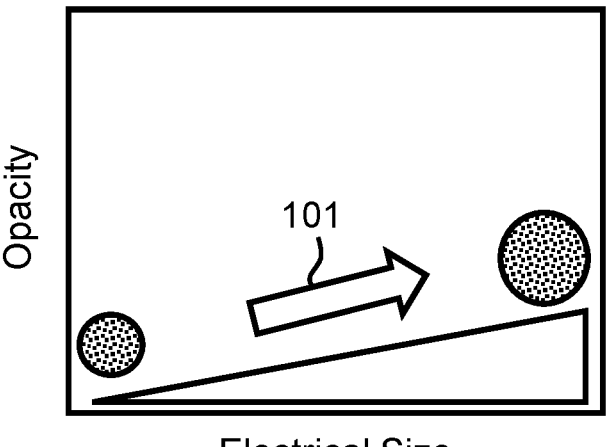
FIGS. 4A to 4C illustrate a method of using EIS-based electrical signatures to determine multiple parameters of cell aggregates according to embodiments of the present disclosure.

Referring to FIG. 4A, a method of the present disclosure includes determining if a cell aggregate has increased in its optical size (i.e., its physical size or the overall diameter/ outer dimensions of the cell aggregate) based on whether there is an increase in the electrical size and concurrently a relatively small or substantially no change in opacity. As illustrated schematically in FIG. 4A, an increase in the electrical size concurrent with a relatively small increase or substantially no change in opacity is indicative of an increase in the optical size of a cell aggregate (101). For example, if more cells have adhered to an existing cell aggregate or if the cells of a spheroid have replicated in a way that increases the optical size of the cell aggregate, it is possible to determine this change by comparing the electrical size of the cell aggregate over time. It would not be necessary to employ conventional methods of extracting the cell aggregate for examination/measurement under the microscope, which may possibly damage or stress the cell aggregate from repeated handling. The present method thus provides a less invasive way of monitoring at least one parameter of cell aggregates.

Figure 4B:
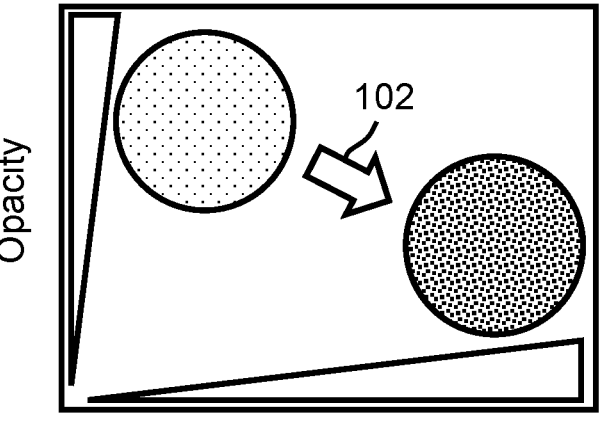

A method of the present disclosure includes determining if cell proliferation has occurred over time in a cell culture based on whether there is a decrease in opacity and concurrently an increase in the electrical size. As illustrated schematically in FIG. 4B, a decrease in the opacity concurrent with an increase in the electrical size is indicative of an increase in the number of cells associated with a cell aggregate (102). For example, when where the cell aggregate is formed in/on a microcarrier, the optical size of a cell aggregate is generally dependent on the size of the microcarrier. The optical size of such a cell aggregate may be substantially the same whether or not the cells in/on the microcarrier have proliferated. The conventional way to determine that cell proliferation has occurred is to dissociate the cell aggregate into individual cells so that the number of cells can be counted. In contrast, the present method is able to quantify a degree of cell proliferation based on electrical signatures derived from impedances alone, without the need to destroy the integrity of the cell aggregate.

Figure 4C:
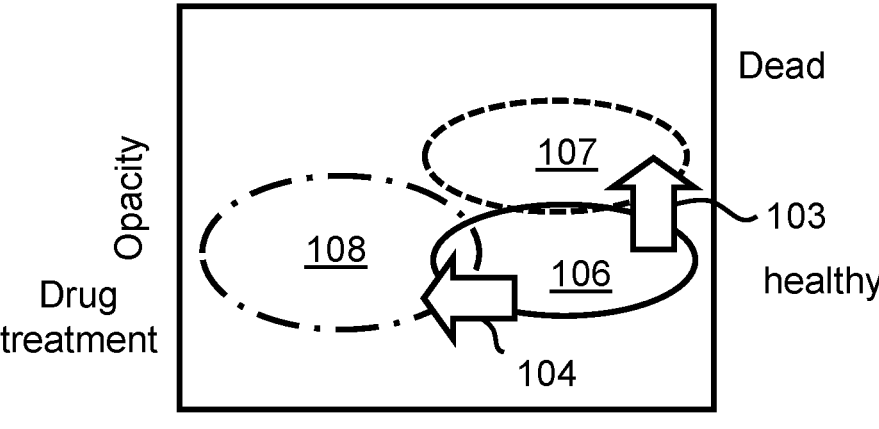

A method of the present disclosure includes determining cell viability or health of the cell aggregate, based on the opacity and/or the electrical size. The method may further include determining cytotoxicity response or drug efficacy based on changes in the opacity and/or electrical size. The method may include comparing changes (if any) in the opacity and the electrical size of the same cell aggregate culture over time. Alternatively, the method may include comparing changes (if any) in the opacity and the electrical size, relative to non-living (dead) reference particles. Alternatively, the method may include comparing changes (if any) before, during and/or after introduction of a drug. Alternatively, the method may include comparing changes (if any) before, during, and/or after one or more cell culture conditions are changed. As illustrated schematically in FIG. 4C, an increase in the opacity concurrent with a decrease or substantially no change in the electrical size may be indicative of a decrease in cell viability (103), a decrease in the proportion of living cells, an increase in the proportion of dead cells, or the health of the cell aggregate. For example, the electrical signatures obtained may change from a range characteristic of healthy cells (106) to a range characteristic of dead cells (107). The increase or decrease in impedance signal can in turn be indicative of the efficacy of a drug or a course of treatment. Also, as illustrated schematically in FIG. 4C, a decrease in electrical size concurrent with a relatively small decrease or substantially no change in the opacity may be indicative of the susceptibility of cells (e.g., cancer tumeroids) to drug treatment (drug susceptibility) (104). For example, the electrical signatures obtained may change from a region characteristic of healthy cells (106) to a region characteristic of cells which have shrunk through dissociation of some but not all of the cells (108).

Experiments were carried out to verify the operability of the methods and devices of the present disclosure. These non-exhaustive and non-limiting examples are described below merely to aid understanding.

Figure 5:
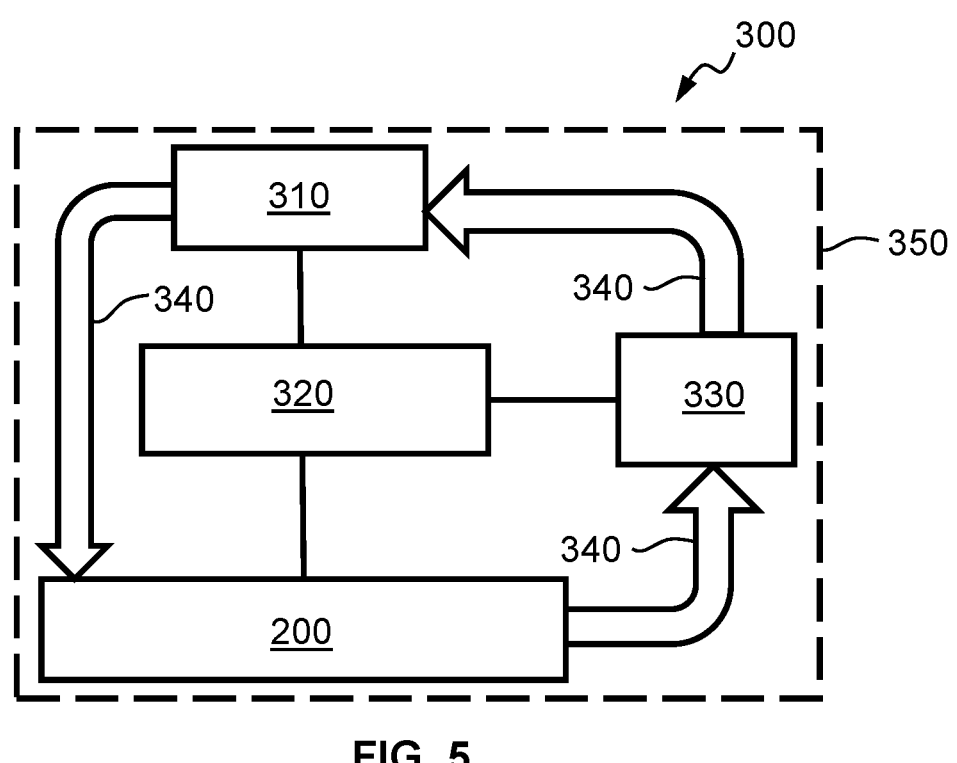
FIGS. 5 and 6 schematically illustrate examples of a monitoring system according to the present disclosure.

FIG. 5 illustrates a system (300) configured according to an embodiment of the present disclosure to monitor cell aggregates on a continuous and real-time basis. The system includes a reservoir (310) in which one or more cell aggregates may be cultured in a culture medium. Examples of the reservoir include but are not limited to a culture flask. The system (300) includes a pump (330), such as a peristaltic pump, to enable a flow of the culture medium from the reservoir (310) to a monitoring device (200), and from the monitoring device (200) back to the reservoir (310), in a continuous closed loop or flow path (340). A controller (320) is coupled to the pump (330) to control a flow rate in the flow path (340). In some examples, the culture medium is pumped at a flow rate of 1 milliliter per minute (mL/min). As the pump (330) operates to enable a flow of the culture medium, some cell aggregates from the reservoir (310) may be carried along in the culture medium to the monitoring device (200). The monitoring device (200) may be a microfluidic chip configured with a channel (212) in fluid communication with the reservoir (310) via the flow path (340). The monitoring device (200) includes a plurality of electrodes (220) disposed across the channel (212), such that the electrodes will be exposed to and in contact with the culture medium flowing through the channel (212). The electrodes (220) are operably coupled to the controller (320) such that EIS signals or impedance-related signals can be obtained from or read across selected electrodes. The cell aggregates are tested or measured as they flow past the electrodes (220), after which the cell aggregates continue on the flow path (340) and return to the reservoir (310) where they can continue growing or changing in the controlled environment provided in the reservoir. In this manner, the system (300) provides flow path that defines a closed recirculating flow of the cell aggregates in a loop configured for dynamic monitoring. The recirculating system is suitable for dynamic monitoring of cell aggregates from the same cell culture over a relatively long period of time (e.g., in terms of weeks or even a number of months). In the present disclosure, "dynamic monitoring" refers to monitoring, testing or collection of data from the subject (in this case, cell aggregates) when the subject is in motion relative to the sensors (in this case, the electrodes). Dynamic monitoring here takes the form of enabling a flow of the culture medium carrying the cell aggregates along a flow path, in which the flow path is configured to intersect at least one set of electrodes. In other words, dynamic monitoring may also be described as obtaining or monitoring impedance-related signals concurrently with the flow path and/or particles disposed therein being in a continuous flow mode. Alternatively, obtaining impedance-related signals when the subject is in motion relative to the sensors (electrodes) include dynamic monitoring. In the present disclosure, "electrical monitoring" and "impedance monitoring" may be used interchangeably to refer to obtaining impedance-related signals.

Since the present method enables cell culture monitoring to be based entirely on EIS-based electrical signatures, human intervention for the purpose of monitoring the cell aggregates (e.g., manual handling and human inspection by optical means) is no longer necessary. The system (300) can thus be configured with a relatively small device footprint, and be configured as part of an incubator (350), such that the entire system can be kept sterile throughout the period required for cell culture. The present system can thus be configured to operate as a self-monitoring incubator suitable for use in bench-scale or in pilot/ramped-up industrial-scale.

Figure 6:
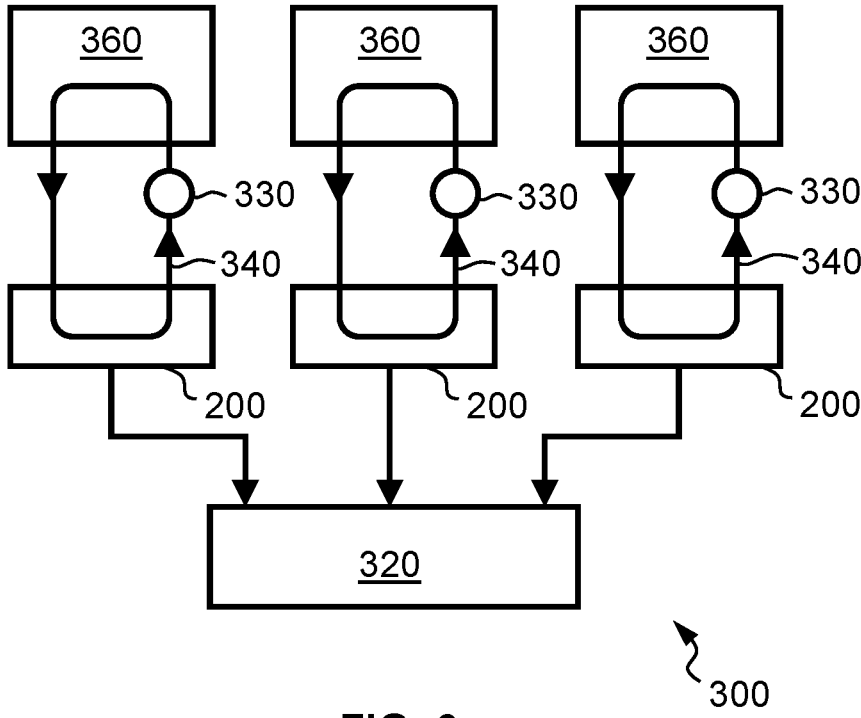

As shown in FIG. 6, the system (300) is scalable by multiplexing the impedance-related signals or the EIS signals from multiple monitoring devices (200), such that multiple industrial-scale bioprocesses in different reservoirs, incubators, or bioreactors (360) can be simultaneously and continuously monitored, round the clock for as long as the entire bioprocess or cell culture process takes. One or more controllers (320) can be configured to collect impedance-related signals from the monitoring devices, determine the respective EIS-based electrical signatures, and determine if one or more parameters of interest are keeping constant or trending in the desired manner. As soon as abnormalities are detected, appropriate actions can be timely taken, e.g., conditions in the bioreactors (e.g., temperature, etc.) may be adjusted. Since the present method obviates the need for fluorescence staining and optical microscopy, or other such destructive or invasive testing techniques, it enables extensive and continuous monitoring to be carried out without negatively impacting the production yield and quality of the production. Another advantage of doing away with optical microscopy is the increased efficiency possible as the present system can be configured to be fully self-monitoring and self-adjusting.

Figure 7A:
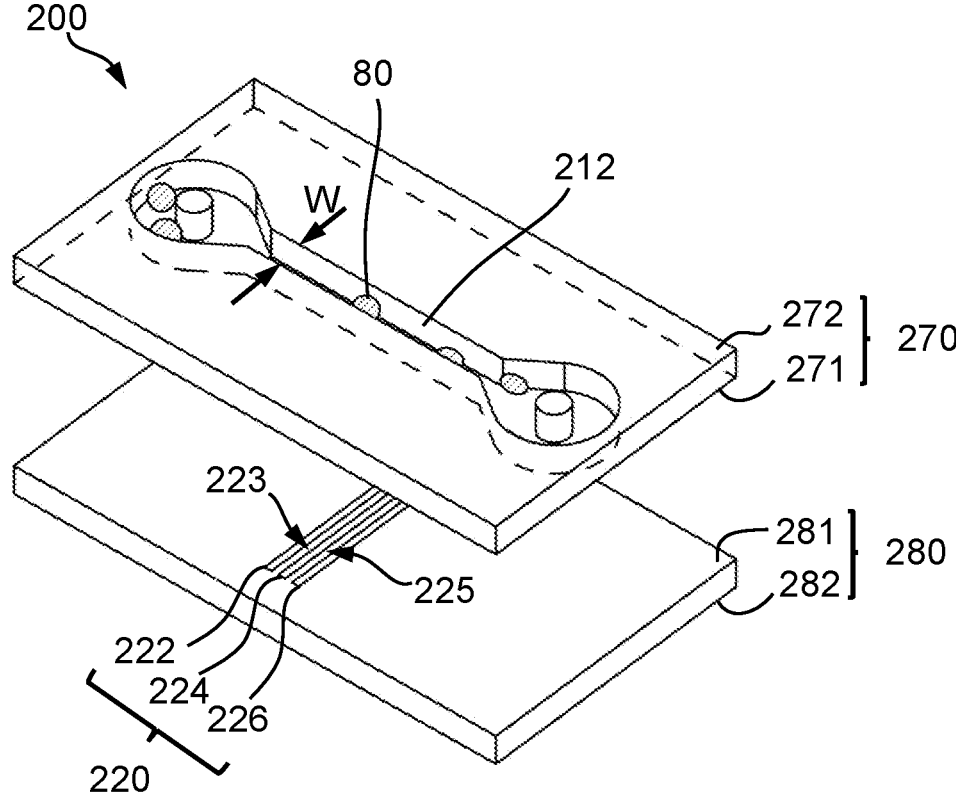
FIGS. 7A and 7B show one embodiment of a monitoring device.
Figure 7B:
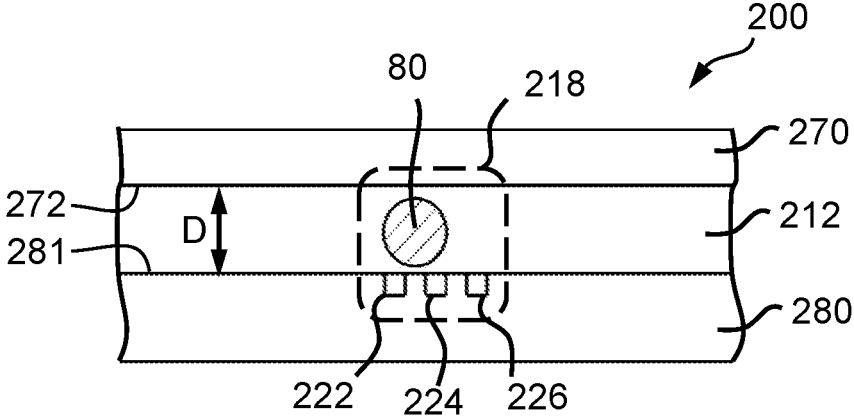

The microfluidic chip may be configured in different variations to suit the type of cell aggregates to be monitored. In some examples, the system (300) may be embodied as an apparatus which can receive interchangeable microfluidic chips. FIGS. 7A and 7B illustrate just one of many possible configurations that may be used as the monitoring device of the present disclosure. FIG. 7A is an exploded perspective view of one example of the monitoring device (200), with an electrode layer (280) and a channel layer (270). For the sake of illustrating the channel (212), the channel layer (270) is shown with the channel-facing side (272) exposed ("upside down"). In assembly, the channel-facing side (272) opposes the electrode-bearing surface (281) of the electrode layer (280) to form the channel (212). FIG. 7B, is a partial cross-section showing electrodes (220) disposed along the electrode layer (212) such that a cell aggregate (80) will come across each of the electrodes in turn when the cell aggregate (80) moves along the channel (212). The electrodes (220) may be configured in various ways. In this example, the electrodes (220) are disposed on a common plane (281) defined by the electrode-bearing surface. The electrodes (220) include a first electrode (222), a source electrode (224), and a second electrode (226) spaced apart from one another and substantially parallel to one another on the common plane (281). The source electrode (224) may be disposed between the first electrode (222) and the second electrode (226). A first gap (223) is defined between the first electrode (222) and the source electrode (244), and a second gap (225) is defined between the source electrode (224) and the second electrode (226). The electrodes (220) may be oriented substantially perpendicular to the microfluidic channel (313) such that a cell aggregate (80) moving through the channel (212) will travel pass each of the first electrode (222), the first gap (223), the source electrode (224), the second gap (225), and the second electrode (226) in sequence. In some examples, the source electrode (224) is substantially equidistant from each of the first electrode (222) and the second electrode (226), i.e., the first gap (223) and the second gap (225) may be of a similar width (Wg). In some other examples, the first gap (223) and the second gap (225) may have different widths.

Figure 8A:
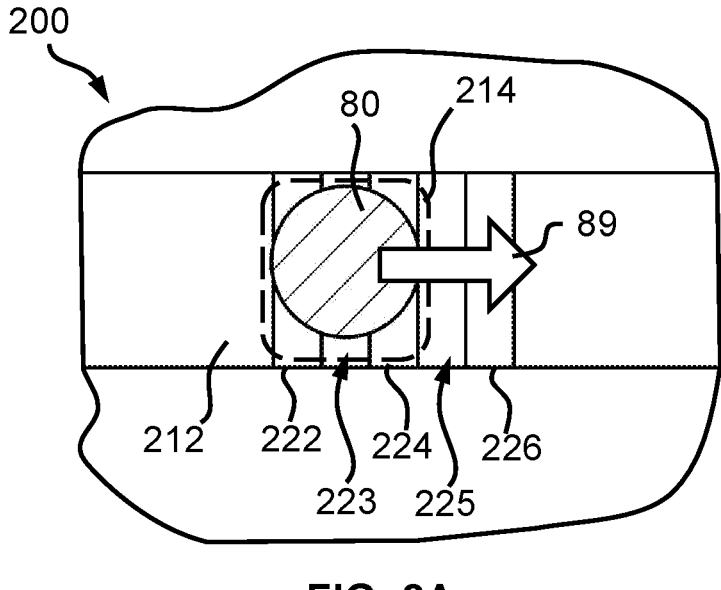
FIGS. 8A and 8B show EIS signals being obtained from a cell aggregate in motion.
Figure 8B:
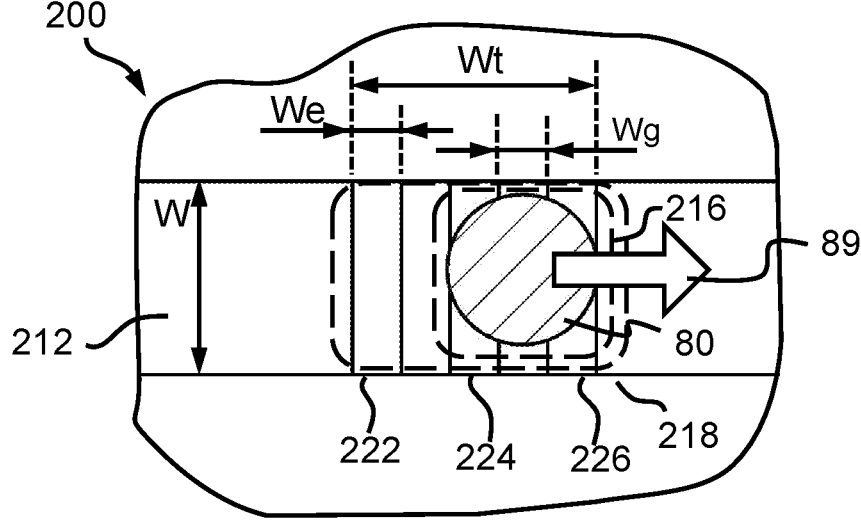

The system is configured to provide a source current to the source electrode (224), and to measure a multi-frequency impedance signal across the source electrode (224) and the first electrode (222), as well as to measure another multi-frequency impedance signal across the source electrode (224) and the second electrode (226). The multi-frequency impedance signals may be measured by sensing impedance-related signals (e.g., current or voltage) at the first electrode (222) and the second electrode (226) respectively. As illustrated in FIG. 8A, the cell aggregate (80) may pass through a first sensing zone (214) where the presence of the cell aggregate can be reflected in the impedance-related signals obtained from the first electrode (222). As shown in FIG. 8B, the cell aggregate (80) may subsequently pass through a second sensing zone (216) where the presence of the cell aggregate can be reflected in the impedance-related signals obtained from the second electrode (226). Collectively, the first sensing zone (214) and the second sensing zone (216) make up a collective sensing zone (218) of the electrodes (220). In some examples, each of the first gap (223) and the second gap (225) may be narrower than a diameter (optical size) of the cell aggregate (80). If an approximate size of the cell aggregate (80) is known, the total width (Wt) of a collective sensing zone (approximated by a sum of the widths of the electrodes and the widths of the gaps therebetween) may be configured to be similar to the diameter (or optical size) of the cell aggregate (80). At the same time, adjacent ones of the electrodes are spaced apart from one another by gaps that are wide enough to enable detectable or distinguishable differential signals to be obtained from the first electrode (i.e., from the first sensing zone) and the second electrode (i.e., from the second sensing zone), with minimum/negligible common mode noise. Preferably, the channel (212) is sized with a width (W) and a depth (D) such that only one cell aggregate may be inside the collective sensing zone (218) at any time instant. In other words, the electrodes (220) and the channel (212) are configured to measure one cell aggregate at a time, with the cell aggregate in motion (89) relative to the electrodes at the time of measurement. In one non-limiting example, if the spheroids or the microcarriers to be tested are in a range of about 200 μm to about 600 μm, the microfluidic channel may be configured with a width (W) of about 1000 μm and a depth (D) of about 600 μm. The electrodes may be configured with a gap width (Wg) of about 200 μm, with each of the electrodes having an electrode width (We) of about 200 μm. Alternatively, for spheroids or microcarriers of about 200 μm, the channel (212) may be configured with a width (W) of 500 μm width and a depth (D) of 300 μm.

The configuration of the electrodes allows for noise reduction in the measurements. When a cell aggregate (80) is in the first sensing zone (214), the impedance-related signal (e.g., current or voltage) measured at the first electrode (222) is representative of the cell aggregate (80), while an impedance-related signal (e.g., current or voltage) measured at the second electrode (226) can be representative of the background noise. A first differential value can be obtained from a difference in the impedance-related signals measured at the first electrode (222) and the second electrode (226). When the cell aggregate (80) moves into the second sensing zone (216) between the second electrode (226) and the source electrode (224), the impedance-related signal (e.g., current or voltage) taken at the second electrode (226) is representative of the cell aggregate (80), while the impedance-related signal (e.g., current or voltage) taken at the first electrode (222) can be representative of background noise. A second differential value can be obtained from a difference between the impedance-related signals measured at the first electrode (222) and the second electrode (226). The first differential value and the second differential value are thus noise-reduced. Examples of EIS signals obtainable from the electrodes include but are not limited to the first differential value, the second differential value, an average of the first and second differential values, etc. Based solely on the EIS signals obtained, the electrical signatures (opacity and/or electrical size) can be determined as described above. As non-limiting examples, the values measured at the first electrode and/or the second electrode include, but are not limited to, voltage signals, current signals, impedance values, reactance values, resistance values, permittivity values, a combination of any of the above, a derivation from any of the above, a derivation from a combination of any of the above, etc. In the present disclosure, these may be referred to generally as impedance-related signals and/or EIS signals.

In another embodiment, the second electrode (226) is disposed relatively further apart from both the first measuring electrode (222) and source electrode (224) such that the impedance-related signals obtainable at the second electrode (226) reflect the background noise at all times throughout the monitoring process.

Figure 9:
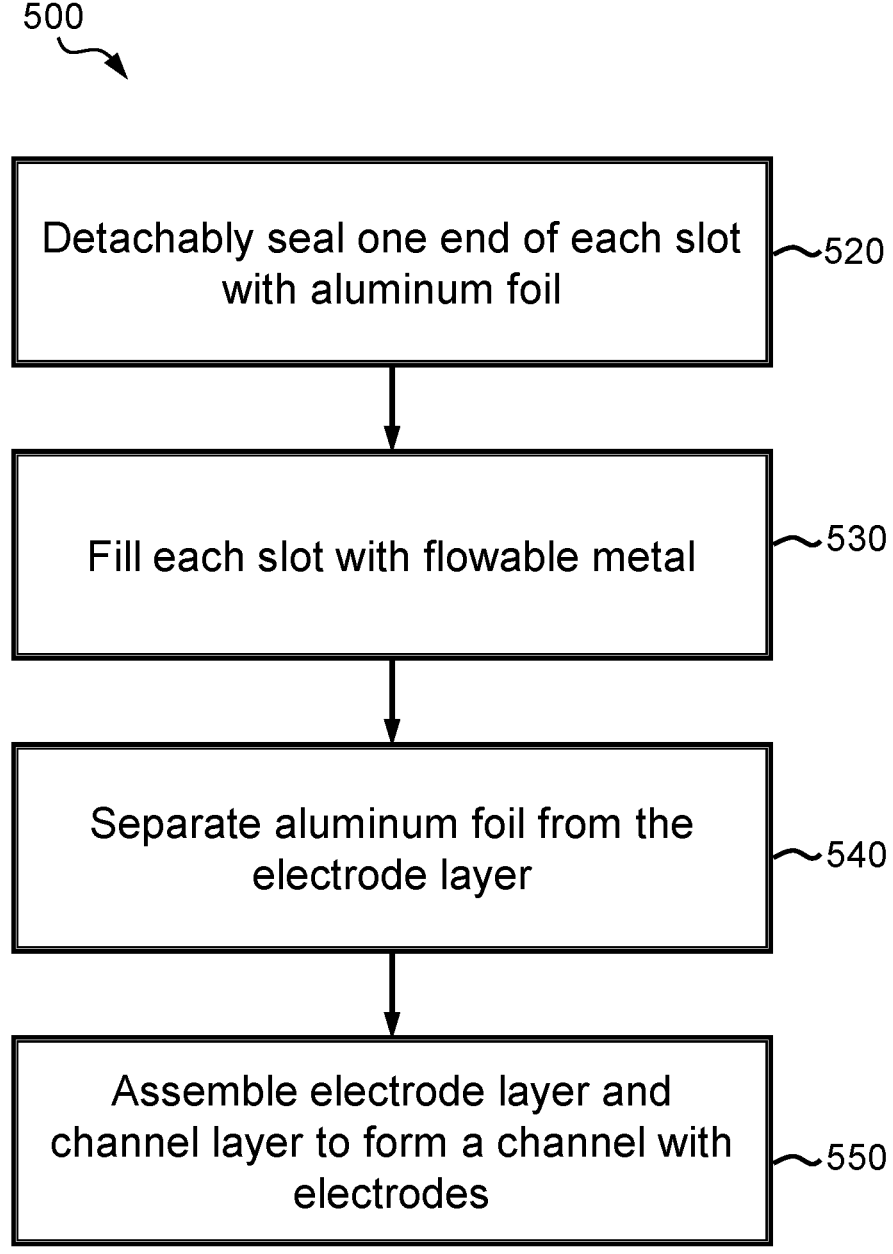
FIG. 9 is a flow chart showing a method of fabricating a microfluidic monitoring device.

Referring to FIG. 9, according to a non-limiting exemplary method (500) of fabricating a microfluidic chip version of the monitoring device (200), a piece of polydimethylsiloxane (PDMS) with a plurality of microscale slots may be fabricated by soft lithography techniques to form an electrode layer (280) of the microfluidic chip. The piece of PDMS may be placed on a heated piece of aluminum foil (520) so as to detachably seal one end of each of the plurality of slots. A metal flowable at a temperature suitable for use with the PDMS is provided. Field's metal (in a flowable state) may be used, for example, to fill the slots (530). Upon solidification of the flowable metal (e.g., Field's metal), a set of electrodes are formed in the electrode layer. The dimensions and spacings of the electrodes can thus be configured by configuring the size, shape, and location of the slots. The aluminum foil is separated from the electrode layer (540) after the set of electrodes are formed. Another piece of PDMS may be fabricated with a groove to serve as a channel layer (270). Assembling the electrode layer with the channel layer forms a channel, with the set of electrodes disposed in the channel. The electrode layer may be sandwiched between the channel layer and a glass layer, with the electrodes (220) aligned with the groove to form the microfluidic channel (550). The microfluidic chip fabricated in this manner is less likely to have metal leakage and has more precisely formed electrodes. Wires can be coupled to respective ends of the electrodes such that one of the electrodes serves as the source electrode and the other two adjacent electrodes serve as the first electrode and the second electrode respectively. The channel extends between an inlet port and an outlet port which can be connected to the rest of the system to complete a flow path. In operation, culture medium carrying cell aggregates flow into the channel via the inlet port and flow out of the channel via the outlet port. The wires may be coupled to an electrical impedance spectroscope, an electrical circuit, and/or a computing device configured to obtain impedance-related signals or EIS signals.

Figure 10A:
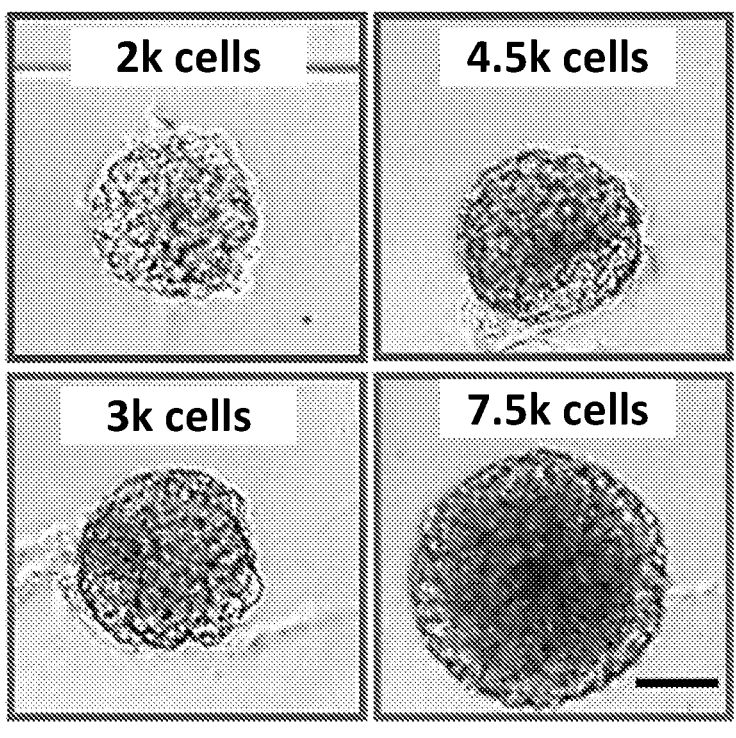
FIG. 10A are images of cell aggregates (spheroids) with different cell-counts.
Figure 10B:
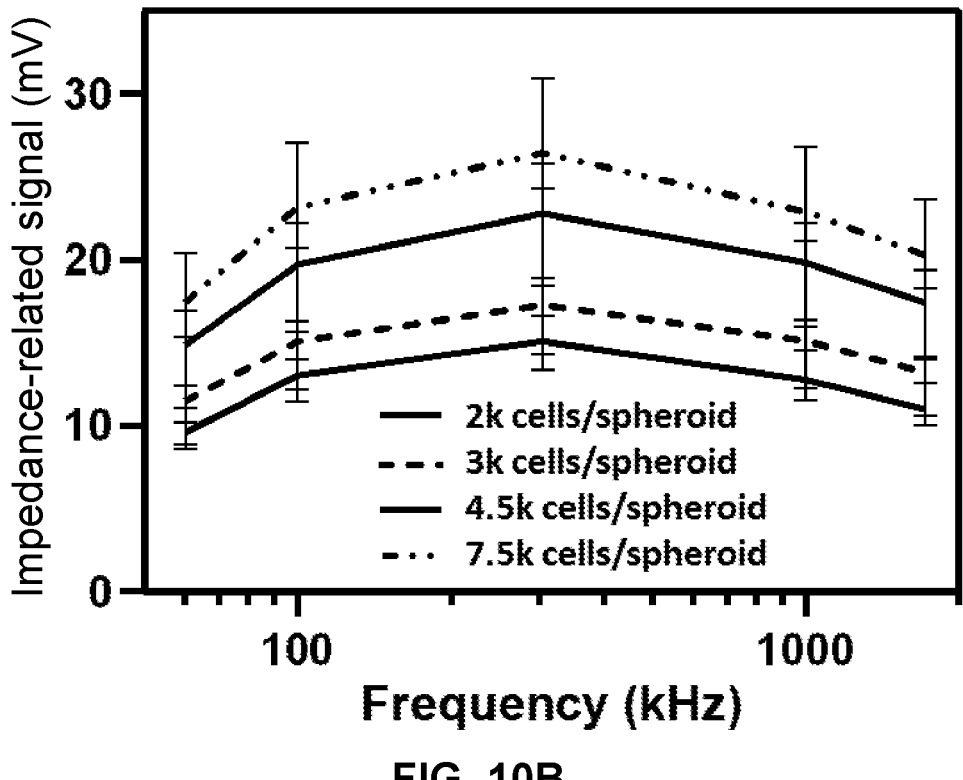
FIG. 10B shows plots of impedance-related signals against frequency for spheroids with different cell-counts.
Figure 11:
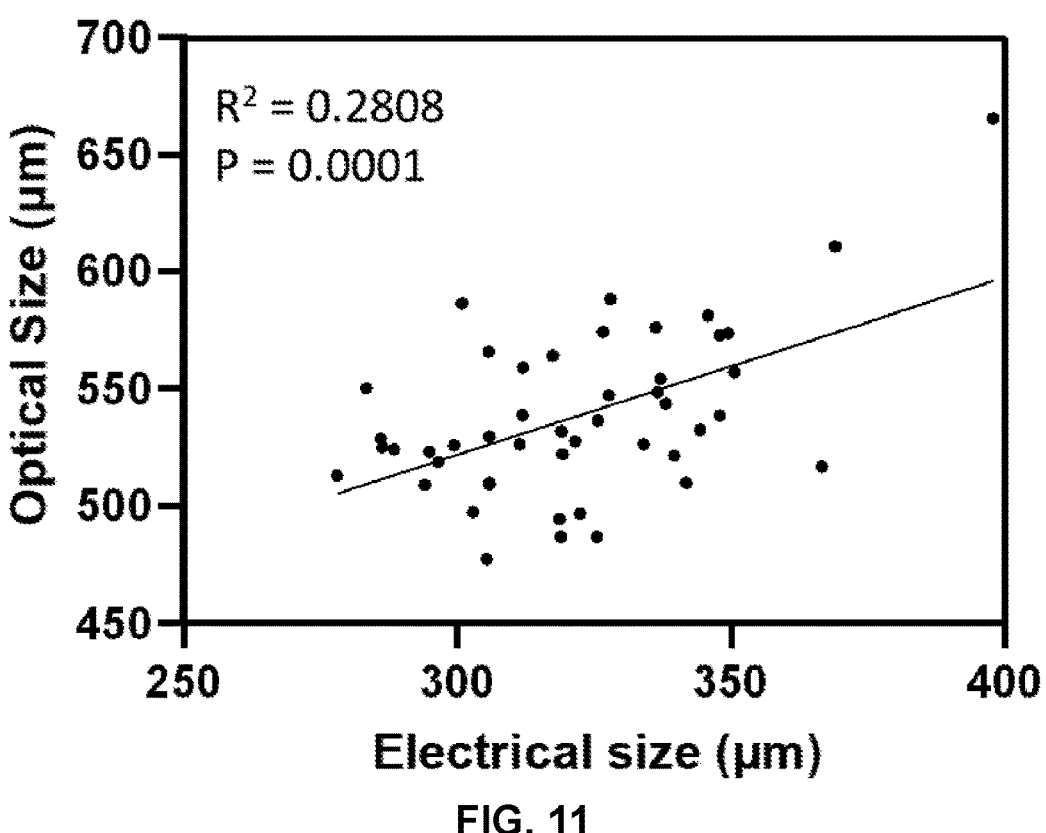
FIG. 11 is a plot of optical size against electrical size.

The following describes various experimental validation of embodiments of the present disclosure. FIG. 10A shows bright field images from high-speed imaging at the same magnification of a cell aggregate (spheroid) with different cell counts, namely, with cell counts of 2000, 3000, 4500, and 7500 respectively. While there is a visible difference between the optical size of the spheroid with a 2000 cell-count and the optical size of the spheroid with a 7500 cell-count, conventional optical methods would not be very helpful for determining if there is any change in the optical size between the spheroid with 3000 cell-count and the spheroid with 4500 cell-count since the changes in optical size are not easily distinguishable. Using an exemplary embodiment of the system proposed herein, the growth of the spheroid (in terms of optical size) can be determined based on EIS-based electrical signatures alone. Impedance-related signals were obtained over a range of excitation frequencies. The resulting plots of impedance-related signals against frequency in FIG. 10B show that, under the same excitation frequency, the electrical size and the optical size are positively correlated. As an improvement over optical inspection, the spheroid with 3000 cell-count and the spheroid with 4500 cell-count can be clearly distinguishable from one another based on the electrical size. In addition, the plots in FIG. 10B show that the electrical size can be used to determine a relative difference or to monitor a change in the number of cells associated with a cell aggregate. FIG. 11 shows a plot of the optical size against the electrical size of the spheroids, in which the optical size is obtained by averaging spheroid diameters in 10 frames to minimize the effects of spheroid orientation when the spheroid flows through the channel. The data obtained indicates a positive correlation between the electrical size and the optical size of a cell aggregate. This validates the method of the present disclosure in which electrical size serves as an EIS-based electrical signature via which one or more physiological or morphological states (e.g., cell aggregate health, growth, etc.) of the cell aggregate may be monitored.

Figure 12:
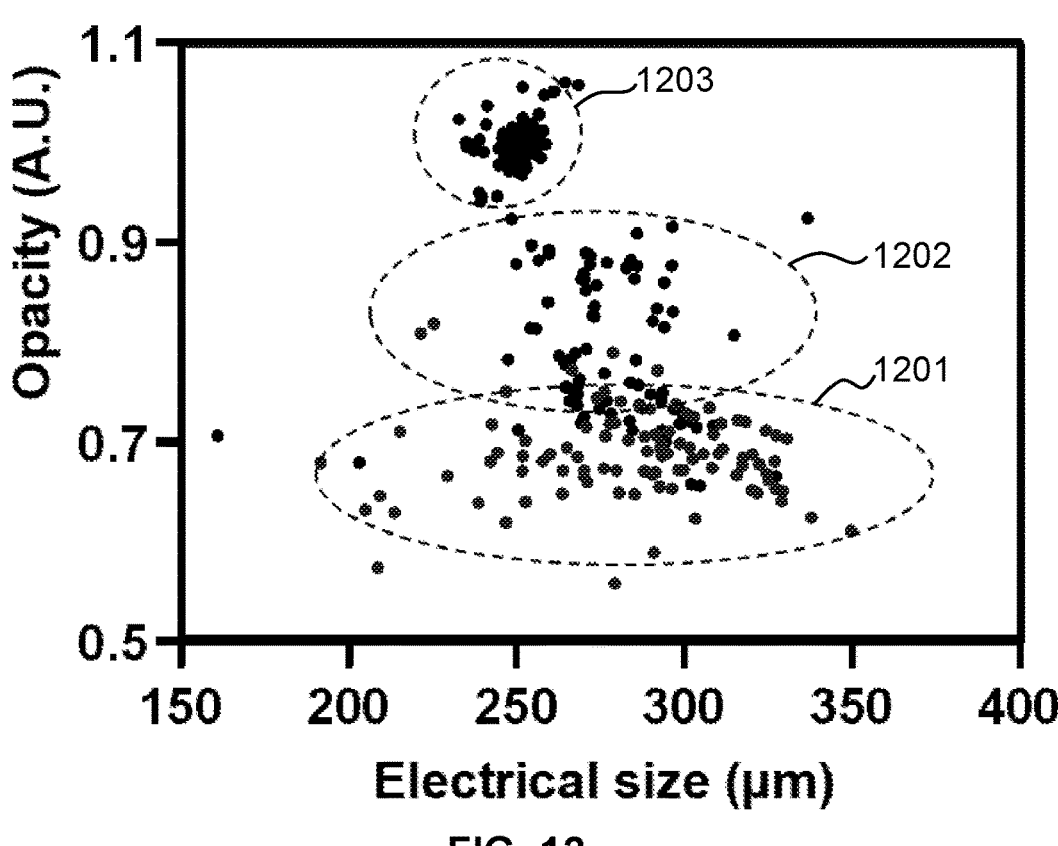
FIG. 12 is a plot of opacity against electrical size.

In another set of experiments, the electrical size and opacity of live spheroids (1201), dead spheroids (1202) (incubated under 75° C. for one hour), and a control (1203) (such as polystyrene beads) are obtained and plotted as shown in FIG. 12. The data shows a significant difference between the opacity of live spheroids (in a region from about 0.5 to about 0.7) and the opacity of dead spheroids (in a region from about 0.7 to about 0.9), while the average electrical size is similar. This validates the method of the present disclosure in which opacity and electrical size are selected to serve as electrical signatures via which one or more physiological or morphological states (e.g., cell viability, etc.) of the cell aggregate can be monitored via monitoring the electrical signatures.

Figure 13:
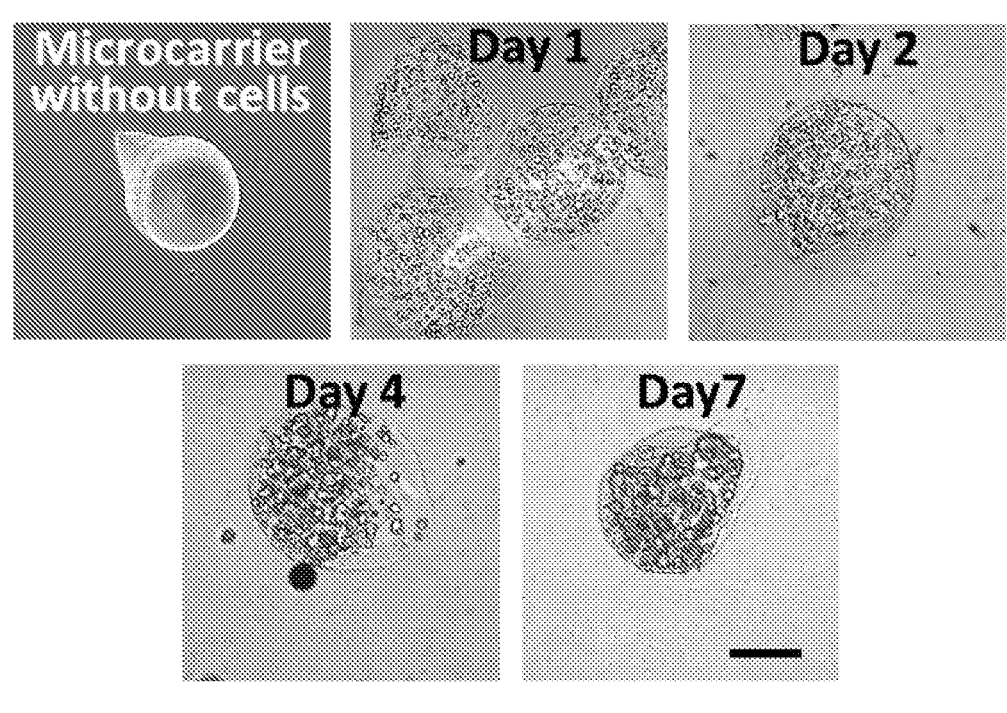
FIG. 13 are images of a cell-encapsulated microcarrier over a period monitored.
Figure 14:
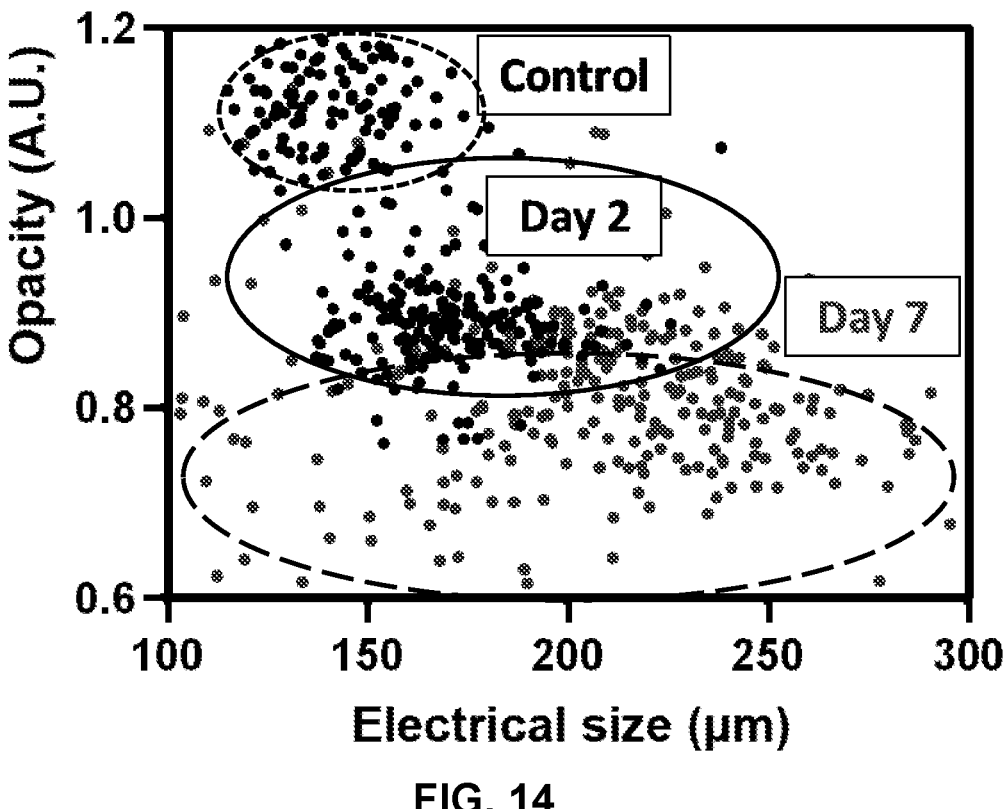
FIG. 14 is a plot of opacity against electrical size over the period monitored for cell-encapsulated microcarriers.
Figure 15A:
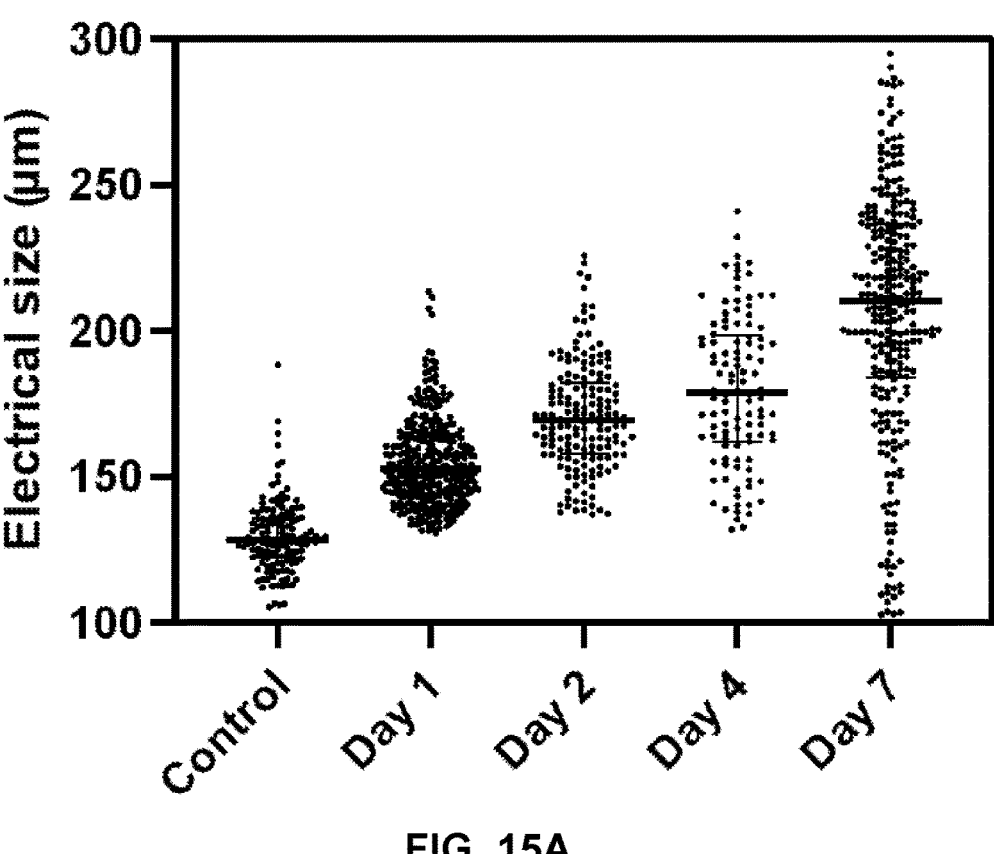
FIGS. 15A and 15B are plots of EIS-based electrical signatures obtained over the period monitored for cell-encapsulated microcarriers.
Figure 15B:
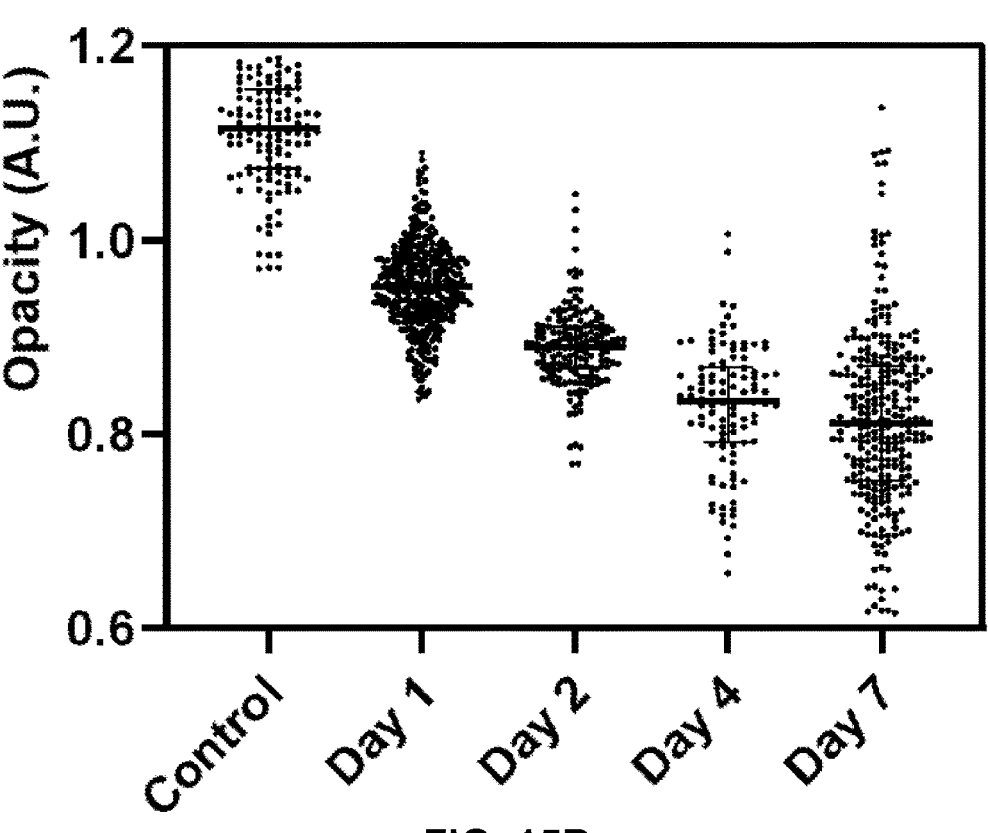

In another set of experiments, the method of the present disclosure is demonstrated to be useful in the continuous monitoring of the physiological and/or morphological changes of a cell aggregate. Keratinocyte cells (HaCaT) in Gelatin methacryloyl (GelMA) hydrogel microcarriers (as an example of a scaffold-free cell-encapsulating hydrogel microcarrier system) are cultured over a period of seven days. As shown in the images of FIG. 13, since the optical size of the microcarrier remains essentially unchanged throughout the seven days, it is highly challenging to determine if there is any change in the number of cells using optical inspection methods without destroying the cell aggregate to perform a cell count. There are however discernable changes in the two EIS-based electrical signatures corresponding to the cell proliferation known to be occurring in the cell culture. As shown in the plot of opacity against electrical size in FIG. 14, both the electrical size and the opacity change from Day 0 (control) to Day 2, and from Day 2 to Day 7. Referring to FIG. 15A and FIG. 15B, more specifically, the mean electrical size increases and concurrently the opacity decreases. This shows that the electrical signatures of the present method are validated for use in non-invasive continuous monitoring to determine cell growth or cell proliferation.

Figure 16A:
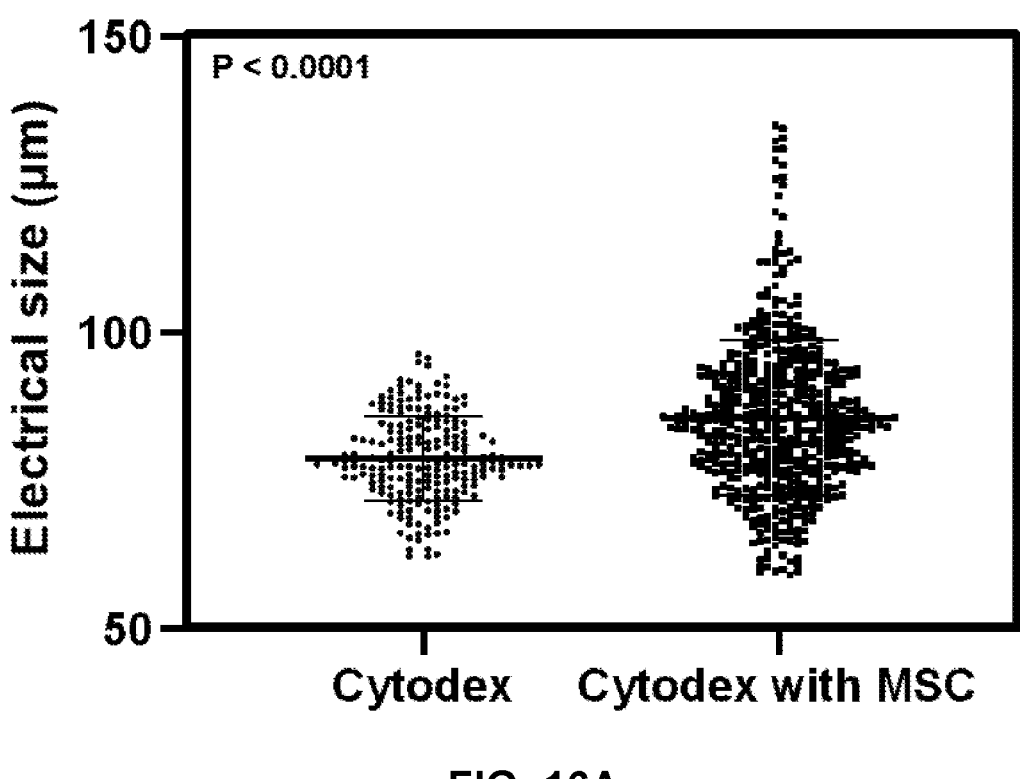
FIGS. 16A and 16B are plots of the EIS-based electrical signatures obtained for cell-adhered microcarriers.
Figure 16B:
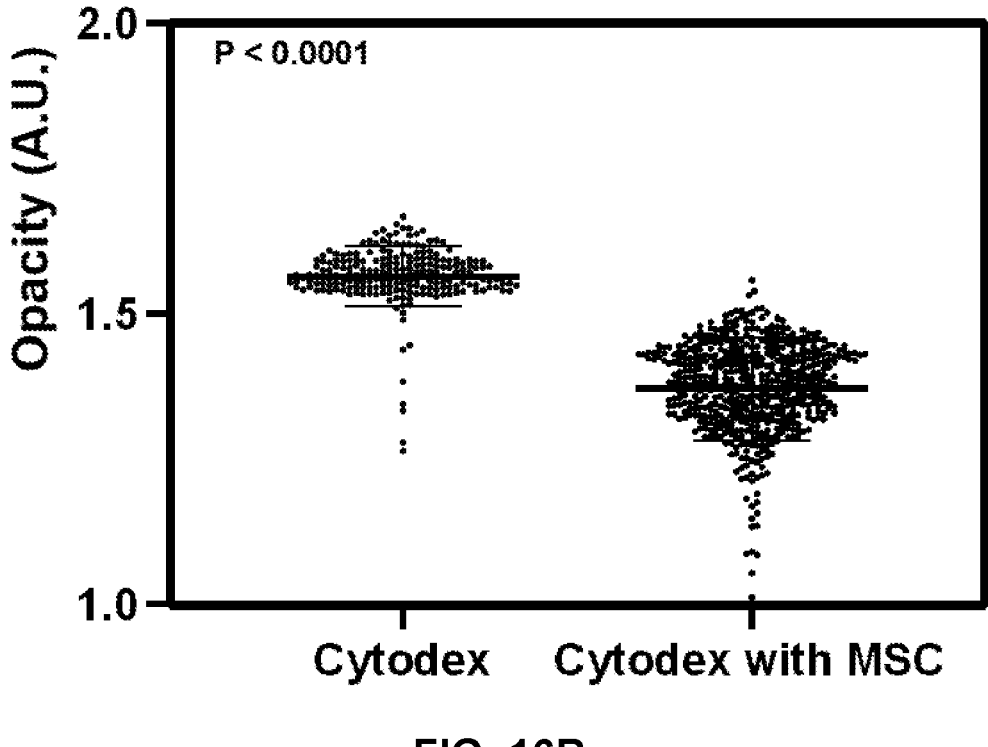

In another set of experiments, as an example of scaffold-based cell aggregates, mesenchymal stem cell (MSC)-attached dextran microcarriers (Cytodex 3) are monitored. As shown in FIG. 16A, the electrical size is higher for the microcarriers with cells adhered thereto than for the microcarriers without cells. As shown in FIG. 16B, the opacity is lower for the microcarriers with cells adhered thereto than for the microcarriers without cells. Collectively, the results described above also indicate the versatility of the system and the EIS-based electrical signatures (electrical size and opacity) in being applicable for multiparametric cell culture monitoring in a variety of different cell culture schemes (e.g., spheroids, scaffold-free microcarriers, hydrogel microcarriers, etc.)

Figure 17A:
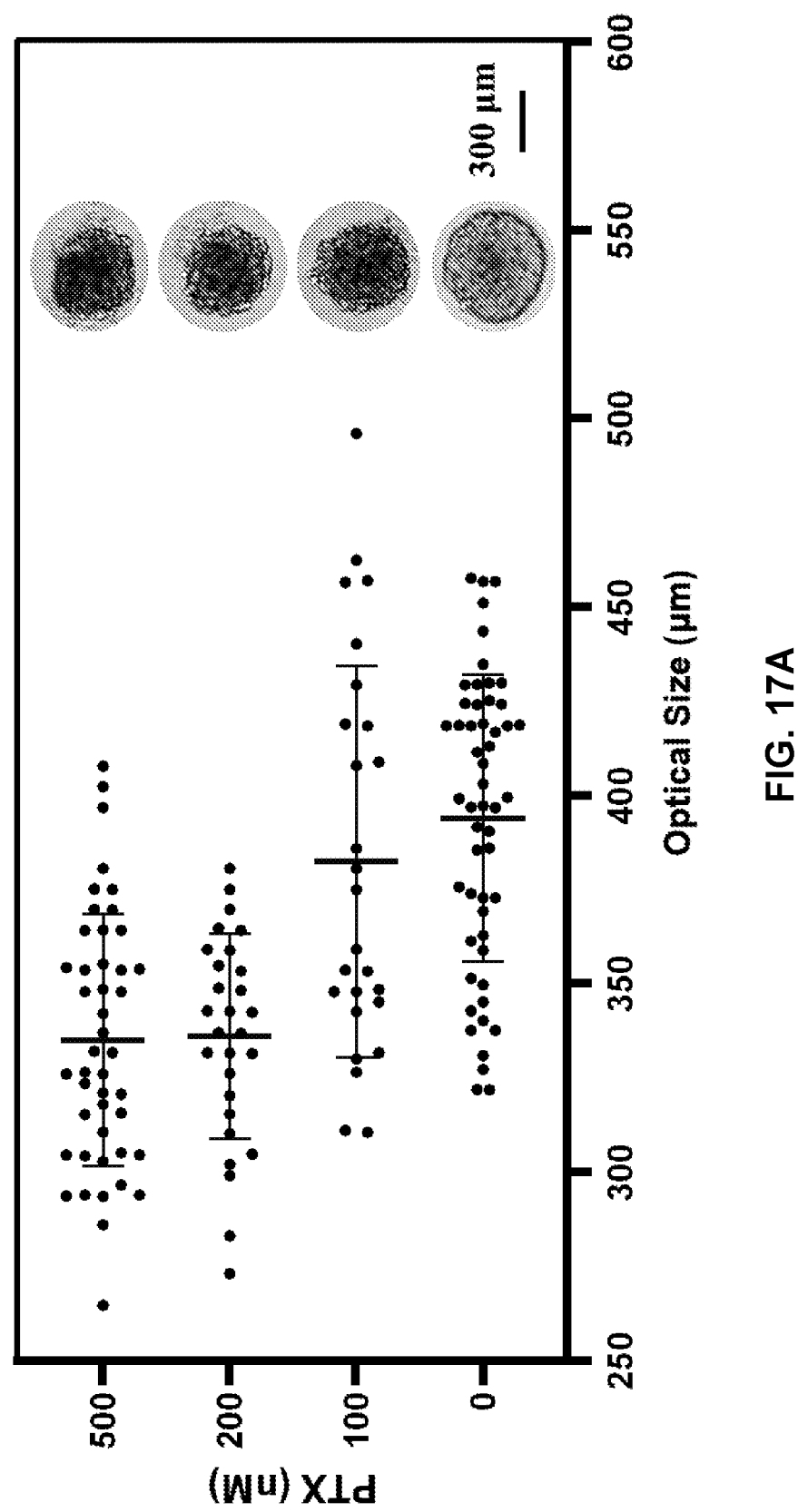
FIG. 17A is a plot of optical sizes of cellular spheroids at different drug concentrations.

In another set of experiments, the method of the present disclosure is shown to be useful in the continuous monitoring of the physiological and/or morphological changes of cell aggregates in drug susceptibility testing. Paclitaxel (PTX), a common anti-cancer drug for several types of cancers, was provided at different concentrations ranging from 0 nM (nanoMole) to 500 nM to cultures of cell aggregates modelling cancer tumoroids and observed over a period of 24 hours. FIG. 17A shows the optical sizes of the cell aggregates, with corresponding brightfield images of exemplary cell aggregates. Based on optical microscopy, it can be appreciated that there are hardly any distinguishable differences between the cell aggregate image at 100 nM of PTX and the cell aggregate images at 200 nM PTX or 500 nM PTX. While optical microscopy may be able to determine that the optical size of the cell aggregate has started to decrease at 100 nM (perhaps through dissociation of some cells at the outer layer of the cell aggregate), it is not adequate for determining physiological changes (or lack thereof) inside the cells remaining in the cell aggregate. Conventionally, it would have required testing the extracel-

US 12,613,179 B2

Figure 17B:
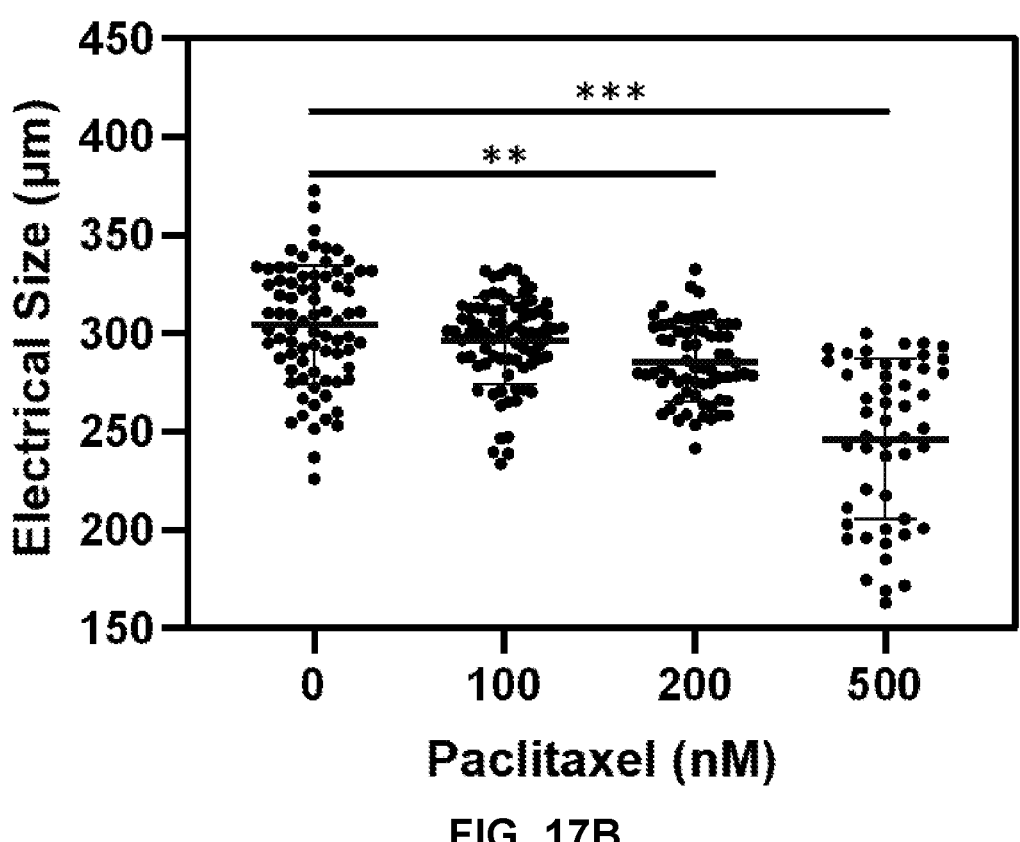
FIGS. 17B and 17C are plots of the EIS-based electrical signatures of cellular spheroids obtained at different drug concentrations.
Figure 17C:
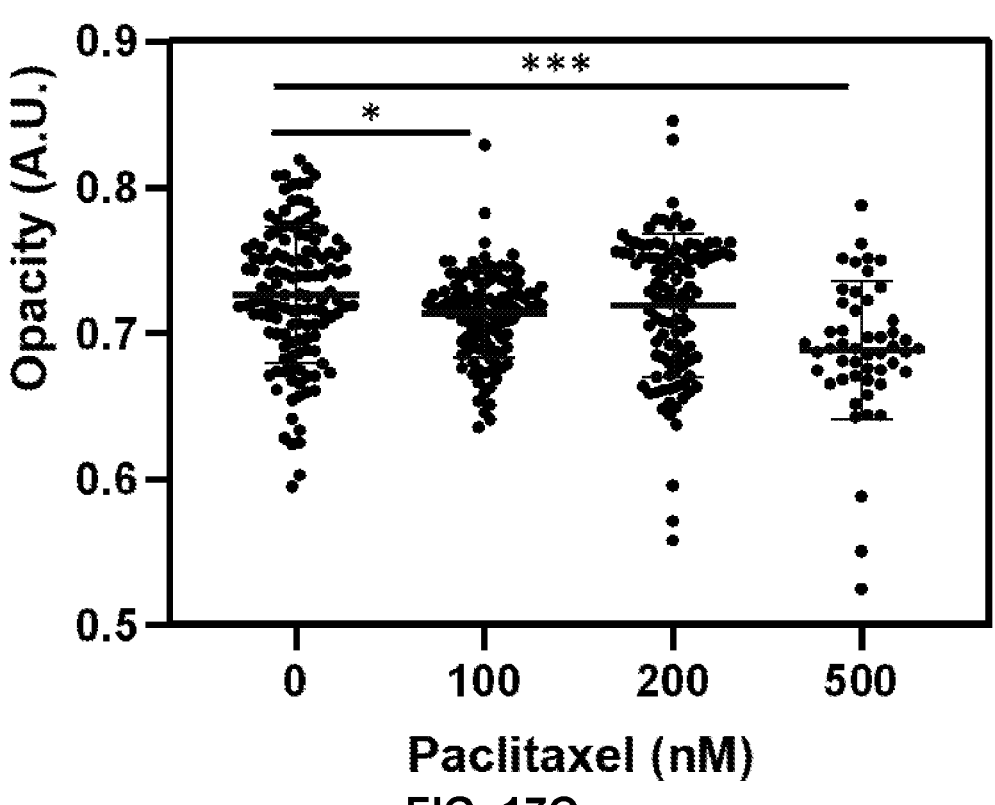
Figure 18:
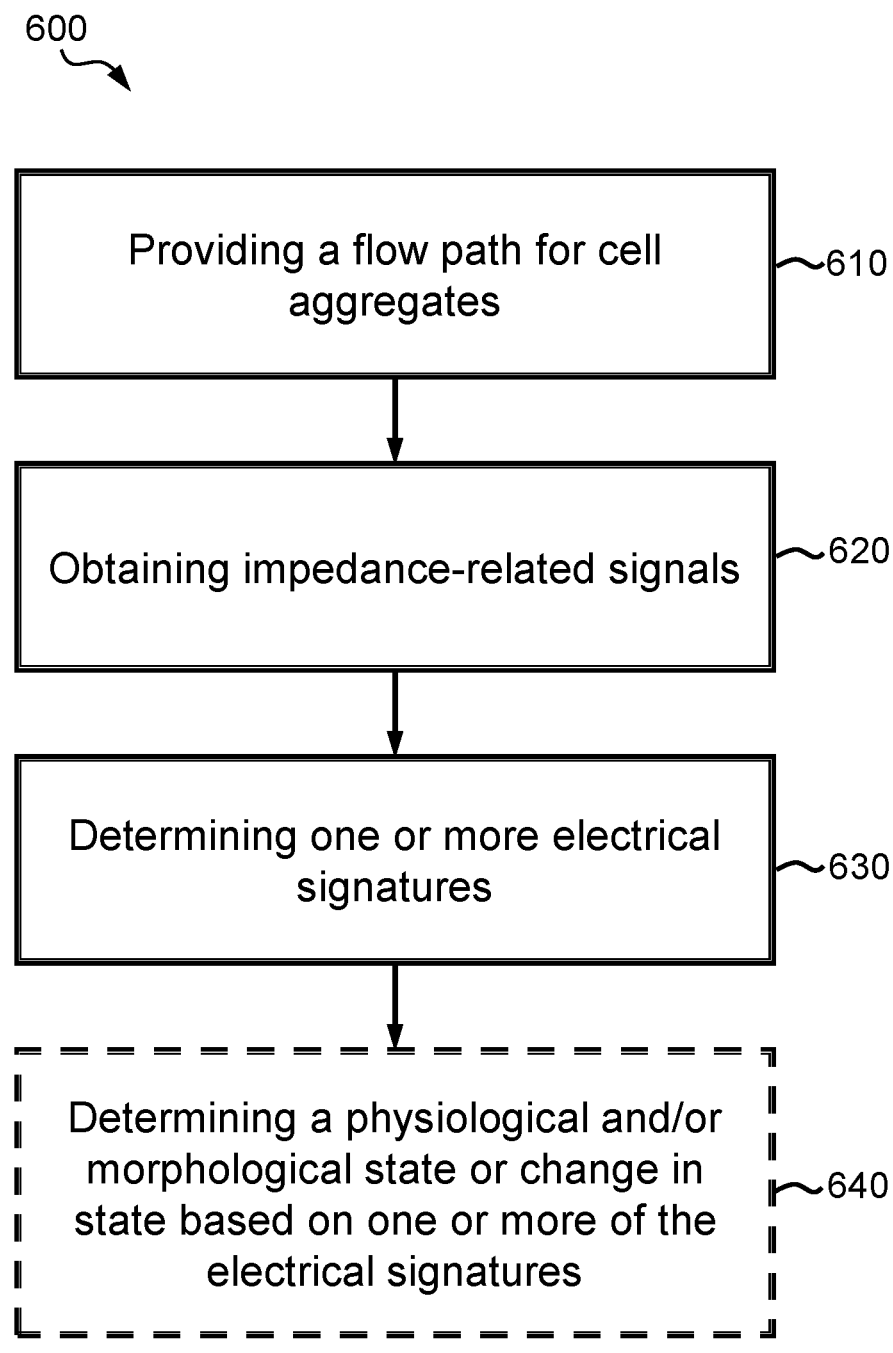
FIG. 18 is a schematic flow chart illustrating a method according to embodiments of the present disclosure.

17 lular environment for metabolites to determine such a change. In contrast, by considering the two EIS-based electrical signatures of electrical size and opacity, more information on the effect of drug treatment can be determined. In particular, the experiments suggest that looking at the electrical size and the opacity offer better insight into the state of cells in the cell aggregate. As shown in FIG. 17B, the electrical sizes of the cell aggregates continue to show a decrease from 300±41.8 µm (0 nM) to 281±40.3 µm as drug concentration was increased to 500 nM. As shown in FIG. 17C, the opacity of the cell aggregates remains relatively unchanged by the increase in drug concentration. The two EIS-based electrical signatures together are able to indicate that the physiological state of the cells undergo substantive changes only after the drug concentration is raised to 500 nM. This is consistent with what is known of the drug treatment modelled in these experiments, and validates the usefulness of the EIS-based electrical signatures in monitoring physiological and/or morphological changes in 3D cell aggregates.

The foregoing describes various embodiments of a method (600) of monitoring one or more cell aggregates. The method includes providing a flow path for the cell aggregates (610) in which the flow path is configured to pass through a collective sensing zone of a set of electrodes. The method includes obtaining impedance-related signals when one of the cell aggregates is in the collective sensing zone (620). The method includes determining one or more electrical signatures based on the impedance-related signals (630) obtained from the set of electrodes. The impedance-related signals are obtained when the cell aggregate is in motion relative to the set of electrodes (dynamic testing). The method includes returning a cell aggregate to the reservoir after the cell aggregate passes through the collective sensing zone. The one or more electrical signatures include opacity and electrical size. The method may further include using one or both of the opacity and the electrical size of one or more cell aggregates to determine a physiological and/or morphological state of the one or more cell aggregate, or to determine a change in the physiological and/or morphological state of the one or more cell aggregates (640). In the present disclosure, for the sake of brevity, determining a state of one or more cell aggregates includes determining one or more physiological and/or morphological states, and/or a change in the one or more states. The state or the change in the state of one or more cell aggregates may be determined based on relative values, trends, changes, differential values, statistical values, etc., of the opacity and/or electrical state.] Embodiments of the present disclosure enable versatile multiparametric, continuous and real-time monitoring in a non-invasive and non-destructive manner. Therefore, in addition to being of practical use as a laboratory technique, the system and method of the present disclosure are also applicable in a wide range of applications, including but not limited to scaled-up industrial bioprocesses, etc., where scalable, label-free (non-destructive) continuous, long term and real-time monitoring is critical to quality assurance and production yield. It can be appreciated that embodiments of the present disclosure may also be used in cases where the cell aggregates are generally planar or two-dimensional, etc.

All examples described herein, whether of apparatus, methods, materials, or products, are presented for the purpose of illustration and to aid understanding, and are not intended to be limiting or exhaustive. Various changes and modifications may be made by one of ordinary skill in the art without departing from the scope of the invention as claimed.

The invention claimed is:

1. A method of monitoring cell aggregates, the method comprising:
providing a flow path of the aggregates in a medium, the flow path being configured to pass through a collective sensing zone of a set of electrodes, wherein the flow path at least partly defines a closed recirculating flow of the cell aggregates in a loop configured for dynamic monitoring;
obtaining impedance-related signals from the collective sensing zone, the impedance-related signals corresponding to each of the medium and one of the cell aggregates in the medium; and
determining one or more electrical signatures for the cell aggregate, wherein the one or more electrical signatures are based on the impedance-related signals obtained from the set of electrodes.

2. The method according to claim 1, wherein the one or more electrical signatures are determined at single-particle resolution.

3. The method according to claim 2, wherein the flow path is configured such that the aggregates are in a continuous flow mode in the collective sensing zone concurrently with the obtaining of the impedance-related signals.

4. The method according to claim 2, wherein the impedance-related signals are obtained when one or more cell aggregates are in motion relative to the set of electrodes.

5. The method according to claim 4, further comprising: returning the one or more cell aggregates to a reservoir after the one or more cell aggregates have passed through the collective sensing zone.

6. The method according to claim 4, wherein the one or more electrical signatures are one or more of an opacity of the one or more cell aggregates and an electrical size of the one or more cell aggregates.

7. The method according to claim 6, wherein the opacity is a ratio between a first impedance and a second impedance, and wherein the first impedance is obtained at a higher frequency than the second impedance.

8. The method according to claim 7, wherein the first impedance and the second impedance are obtained at a beta dispersion range of frequencies.

9. The method according to claim 7, wherein a second frequency is selected from a range of frequencies corresponding to impedance-related signals of the medium such that the second frequency corresponds to a minimum electrical double layer (EDL) effect.

10. The method according to claim 7, wherein the electrical size is determined based on the second impedance.

11. The method according to claim 6, wherein the one or more electrical signatures are EIS-based (electrical impedance spectroscopy-based) electrical signatures.

12. The method according to claim 11, wherein the one or more EIS-based electrical signatures are obtained from differential values between impedance-related signals measured at a first electrode and a second electrode, wherein the first electrode and the second electrode are selected from the set of electrodes.

13. The method according to claim 12, wherein the cell aggregate is in one of a first sensing zone and a second sensing zone, the first sensing zone being provided by the first electrode and a source electrode, the second sensing zone being provided by the second electrode and the source electrode, and wherein the first sensing zone and the second sensing zone form the collective sensing zone.

14. The method according to claim 6, further comprising performing any one or more of the following:

(i) determining a state or a change in the state of the one or more cell aggregates based on the one or more electrical signatures, wherein the state includes a physiological and/or morphological state of the one or more cell aggregates;

(ii) determining a change in an optical size of the one or more cell aggregates based on the one or more electrical signatures;

(iii) determining a change in a cell count of the one or more cell aggregates based on the one or more electrical signatures;

(iv) determining a cell aggregate growth of the one or more cell aggregates based on the one or more electrical signatures;

(v) determining a change in cell viability of the one or more cell aggregates based on the one or more electrical signatures;

(vi) determining a change in health of the one or more cell aggregates based on the one or more electrical signatures;

(vii) determining a cytotoxicity response of the one or more cell aggregates based on the one or more electrical signatures;

(viii) determining a drug efficacy with respect to the one or more cell aggregates based on the one or more electrical signatures.

15. The method according to claim 6, the method comprising:

determining if the cell aggregate has increased in its optical size based on whether there is an increase in the electrical size and whether there is concurrently a relatively small change or no change in the opacity.

16. The method according to claim 6, the method comprising:

determining if cell proliferation has occurred in the cell aggregate based on whether there is a decrease in the opacity and whether there is concurrently an increase in the electrical size.

17. The method according to claim 6, the method comprising:

determining a decrease in cell viability based on whether there is an increase in the opacity and whether concurrently there is a decrease or no change in the electrical size, wherein the cell viability corresponds to one or more of the following: a decrease in a proportion of living cells, an increase in a proportion of dead cells, and a deterioration in a health of the cell aggregate.

18. The method according to claim 6, the method comprising:

determining drug susceptibility with respect to the cell aggregate based on whether there is a decrease in electrical size concurrent with a relatively small decrease or no change in the opacity.

19. The method according to claim 1, wherein the cell aggregate is a spheroid, an encapsulated microcarrier, or a cell-adhered microcarrier.

20. A system for monitoring one or more cell aggregates according to the method of claim 1, the system comprising:

at least one reservoir configured to culture the one or more cell aggregates;

at least one monitoring device having a set of electrodes configured to define a collective sensing zone; and a flow path defining a closed recirculating flow of the one or more cell aggregates in a medium between one of the at least one reservoir and the collective sensing zone of a corresponding one of the at least one monitoring device, the flow path being configured to pass through the collective sensing zone, wherein the at least one monitoring device is configured to obtain impedance-related signals from the collective sensing zone, the impedance-related signals corresponding to each of the medium and one of the one or more cell aggregates in the medium; and determine one or more electrical signatures for the cell aggregate, wherein the one or more electrical signatures are based on the impedance-related signals obtained from the set of electrodes.

* * * * *